(12) United States Patent
Park et al.

(10) Patent No.: US 10,294,204 B2
(45) Date of Patent: May 21, 2019

(54) FLUORESCENCE COMPOUNDS AND PREPARATION METHOD THEREOF

(71) Applicant: BioActs Co., Ltd., Incheon (KR)

(72) Inventors: Jin Woo Park, Incheon (KR); Su-Jung Jang, Gyeonggi-do (KR); Kiwon Kim, Incheon (KR); Gyeong Rim Shin, Incheon (KR); Bongkyu Lee, Gyeonggi-do (KR)

(73) Assignee: BIOACTS CO., LTD., Incheon (KR)

( * ) Notice: Subject to any disclaimer, the term of this patent is extended or adjusted under 35 U.S.C. 154(b) by 0 days.

(21) Appl. No.: 15/497,372

(22) Filed: Apr. 26, 2017

(65) Prior Publication Data

US 2017/0313883 A1 Nov. 2, 2017

(30) Foreign Application Priority Data

Apr. 27, 2016 (KR) .................. 10-2016-0051466
Apr. 12, 2017 (KR) .................. 10-2017-0047199

(51) Int. Cl.
*G01N 21/31* (2006.01)
*C09B 7/02* (2006.01)
*C07D 209/10* (2006.01)
*C07D 251/50* (2006.01)
*C09B 23/06* (2006.01)
*C09B 23/08* (2006.01)

(52) U.S. Cl.
CPC .......... *C07D 209/10* (2013.01); *C07D 251/50* (2013.01); *C09B 23/06* (2013.01); *C09B 23/083* (2013.01); *C09B 23/086* (2013.01); *G01N 2021/3155* (2013.01)

(58) Field of Classification Search
CPC ...... C09B 23/06; C09B 23/083; G01N 23/31; C07D 209/10; C07D 251/50
See application file for complete search history.

(56) References Cited

U.S. PATENT DOCUMENTS

2011/0171678 A1* 7/2011 Leung ................ A61K 41/0057
435/29

FOREIGN PATENT DOCUMENTS

CN 101029179 9/2007
KR 1020110033454 3/2011

* cited by examiner

*Primary Examiner* — Zohreh A Fay
(74) *Attorney, Agent, or Firm* — Duane Morris LLP; Gregory M. Lefkowitz; Jason M. Nolan

(57) ABSTRACT

Provided is a fluorescent compound represented by the following [Chemical Formula 1] and a method for preparing the same:

[Chemical Formula 1]

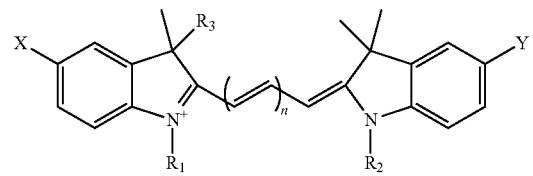

wherein each of X, Y, $R_1$, $R_2$, $R_3$ and n is the same as defined in the specification.

13 Claims, 7 Drawing Sheets

FLUORESCENCE COMPOUNDS AND PREPARATION METHOD THEREOF

CROSS-REFERENCE TO RELATED APPLICATIONS

This application claims priority under 35 U.S.C. § 119 to Korean Patent Applications 10-2016-0051466 and 10-2017-0047199, filed on Apr. 27, 2016 and Apr. 12, 2017, respectively, in the Korean Intellectual Property Office, the disclosure of which is incorporated herein by reference in its entirety.

TECHNICAL FIELD

The following disclosure relates to a fluorescent compound. More particularly, the following disclosure relates to a cyanine-based fluorescent compound including an alkylcarboxyaminocyanuric chloride substituent and application thereof.

BACKGROUND

Since a biosubstance itself shows little or no fluorescence in the visible light or near infrared region, imaged data have been obtained in the field of bioscience through various methods using a biosubstance and a fluorescent dye or a specific biosubstance including a biosubstance preliminarily labeled with a fluorescent dye in combination with an optical system in order to observe a biological phenomenon in a cellular stage or sub-cellular stage in vivo or in vitro, or to carry out laparography and to obtain an optical image of a diseased site through the projection in vivo.

Various optical analysis systems used in the field of bioscience use a selected fluorescent dye having an excitation wavelength and emission wavelength suitable for the observation of fluorescence depending on the light source and filter embedded therein, as a fundamental material or reagent.

Known optical analysis systems used frequently include those for research, such as a fluorescence microscope for observing cells, confocal microscope, flowcytometer, microarray, qualitative polymerase chain reaction (PCR) system, electrophoresis system for isolation and analysis of nucleic acids and proteins and a realtime in vivo imaging system; and those for diagnosis and treatment, such as an in vitro diagnosis system based on a nucleic acid and protein diagnosis kit (or biochip) combined with immunoassay or PCR analysis and statistical technology, a surgery die for image-guided surgery and an endoscope system. In addition, systems for use in novel applications and having a higher level of resolution and data processing capability have been developed continuously.

In general, most fluorescent dyes for use in labeling of a biomolecule, such as protein or peptide, include a structure such as anthranilate, 1-alkylthic isoindole, pyrrolinone, bimane, benzoxazole, benzimidazole, benzofurazan, naphthalene, coumarin, cyanine, stilbene, carbazole, phenanthridine, anthracenes, bodipy, fluorescein, eosin, rhodamine, pyrene, chrysene or acridine.

When screening a fluorescent dye structure applicable to the field of bioscience among the above mentioned fluorescent chromophores, it is generally important that most biosubstances emit strong fluorescence in a medium, i.e., aqueous solution and water-soluble buffer, containing the same and have an excitation wavelength and fluorescence wavelength suitable for a fluorescence device.

It is required for a dye mainly applicable to the field of bioscience to cause less photobleaching and quenching in aqueous solution or under a hydrophilic condition, to have a large molar extinction coefficient so that it may absorb a large amount of light, to be in the visible region or near infrared region of 500 nm or more away from the fluorescence region of a biosubstance itself, and to be stable under various pH conditions. However, there is a limitation in the structure of a dye applicable to labeling of a biosubstance while satisfying the above requirements.

Chromogens which meet the above requirements include cyanine, rhodamine, fluorescein, bodipy, coumarine, acridine and pyrene derivatives. In addition, such a dye may be used alone or a reactive group may be introduced thereto so as to be bound with a specific substituent in a biomolecular structure. Currently, xanthane-based fluoresceins and rhodamins and polymethine-based cyanine derivative dye compounds have been commercialized largely.

Particularly, a dye compound having a cyanine chromophore is advantageous in that it facilitates synthesis of compounds with various absorption/excitation wavelengths. In addition, such a dye compound has many advantages as follows and thus is used frequently for biological applications. It generally has excellent optical stability and pH stability, shows a narrow absorption and emission wavelength range, has a fluorescence region of 500-800 nm, which is not overlapped with the fluorescence region of a biomolecule itself, and allows easy analysis, and shows a high molar extinction coefficient with a slight difference depending on solvents and solubility characteristics.

Further, a dye compound having a cyanine chromophore may be used advantageously for an optical filter for an image display device or a resin composition for laser welding. A compound which shows high-intensity absorption to specific light has been used widely for an optical filter for an image display device, such as a liquid crystal display device, plasma display panel, electroluminescence display, cathode tube display device or a fluorescence display tube, or for an optical element of an optical recording medium such as DVD±R. It is required for an optical filter to have a function of selectively absorbing light with an undesired wavelength. In addition to this, it is required to absorb light with a wavelength of 480-500 nm and 540-560 nm in order to prevent reflection of external light, such as light from a fluorescence lamp, or glare. Further, it is required to have a function of selectively absorbing light with a wavelength in the near infrared region in order to improve the quality of an image.

Thus, there has been a continuous need for developing a novel dye having excellent optical stability and pH stability and showing a high molar extinction coefficient with a narrow absorption/emission wavelength range in a specific wavelength region so that it may be applied advantageously to various industrial fields.

SUMMARY

An embodiment of the present disclosure is directed to providing a fluorescent compound, which has excellent optical stability and pH stability, shows a narrow range of absorption and emission wavelengths and provides improved fluorescence intensity in a fluorescence region of 600-800 nm so that it may be used as a contrast medium composition, and particularly contains a cyanuric chloride substituent to enhance fluorescence, as well as a method for preparing the compound and application of the compound.

To accomplish the above object, in one aspect, there is provided a fluorescent compound represented by [Chemical Formula 1] and a method for preparing the same.

[Chemical Formula 1]

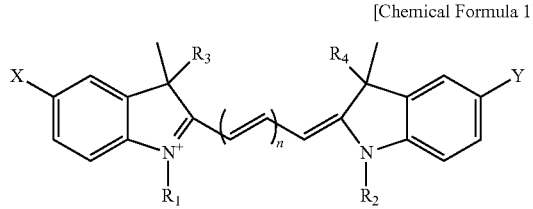

wherein X and Y are the same or different, and each is independently selected from H, —$SO_3^-$ and —$SO_3H$;

$R_1$ and $R_2$ are the same or different, and each is selected from $C_{1-7}$ alkyl, $C_{8-18}$ alkyl, —$(CH_2)_mSO_3^-$, —$(CH_2)_mSO_3H$, and

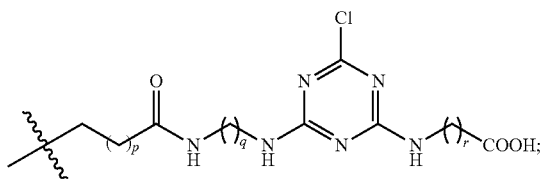

$R_3$ and $R_4$ are the same or different, and each is selected from $C_{1-7}$ alkyl, —$(CH_2)_mCOOZ_1$ and

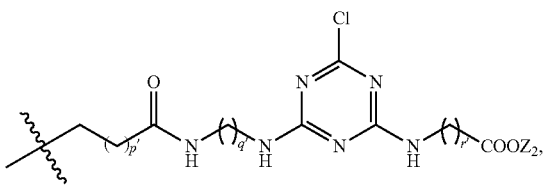

with the proviso that both of $R_3$ and $R_4$ cannot represent any one selected from —$(CH_2)_mCOOZ_1$ and

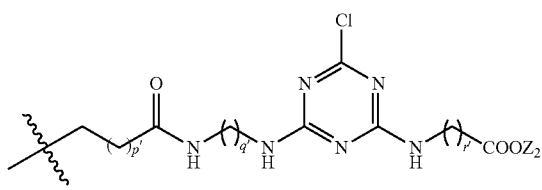

at the same time;

$Z_1$ and $Z_2$ are the same or different, and each is independently substituted with a substituent selected from H, N-succinimidyl, hydrazinyl, N-hydroxysuccinimidyl, N-hydrosuccinimidyloxy, sulfosuccinimidyloxy, 4-sulfo-2,3,4,5-tetrafluorophenyl, maleinimide$C_{0-10}$alkylaminyl, vinylsulfonyl, vinylsulfonyl$C_{0-6}$alkylaminyl and amino $C_{0-6}$alkyl;

n is an integer of 1-6;
m is an integer of 1-7;
p is an integer of 1-10;
q is an integer of 0-6;
r is an integer of 1-10;
m' is an integer of 1-7;
p' is an integer of 1-10;
q' is an integer of 1-10; and
r' is an integer of 1-10.

According to an embodiment, at least one of $R_1$ and $R_2$ may be

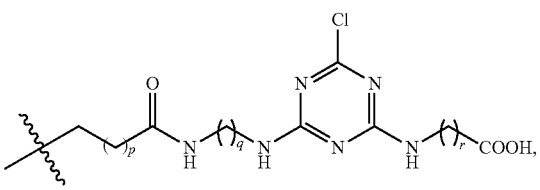

and at least one of $R_3$ and $R_4$ may be any one selected from $(CH_2)_mCOOZ_1$ and

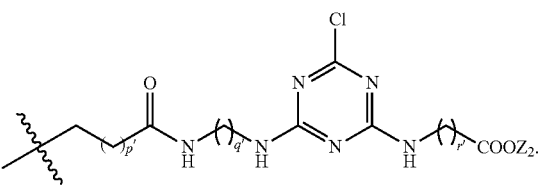

In another aspect, there is provided a contrast medium composition including the fluorescent compound represented by [Chemical Formula 1] as an active ingredient.

In still another aspect, there is provided a method for labeling a target material with the fluorescent compound represented by [Chemical Formula 1].

The fluorescent compound disclosed herein has high stability in an aqueous condition and thus may be stored for a long time with ease. In addition, the fluorescent compound disclosed herein has a cyanuric chloride substituent introduced thereto and shows improved fluorescence intensity even at a lower concentration as compared to the conventional structure, and thus may be used more effectively for labeling and dyeing a target material. Further, the fluorescent compound disclosed herein has excellent optical stability to show stable fluorescence even when used for long-term dyeing, shows excellent fluorescence intensity while not being accumulated in the body after its administration, and thus carries out dyeing and in vivo imaging with ease even in a smaller amount as compared to the conventional dyes, thereby providing high cost efficiency.

DETAILED DESCRIPTION OF EMBODIMENTS

Figure 1:
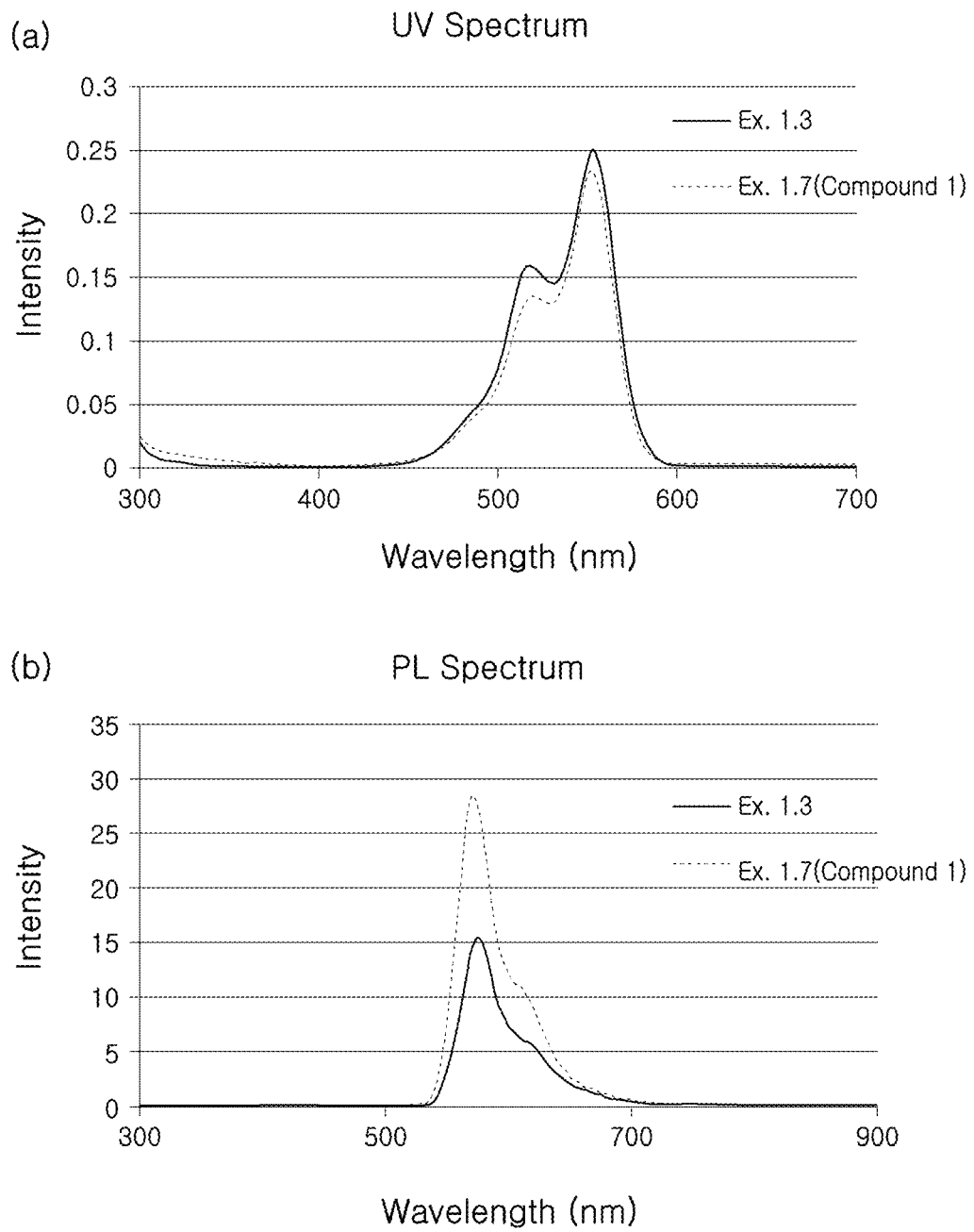
FIG. 1 shows the results of evaluation of optical properties depending on the introduction of an alkylcarboxyaminocyanuric chloride substituent according to an embodiment.

Hereinafter, various aspects and embodiments of the present disclosure will be explained in more detail.

In one aspect, there is provided a fluorescent compound represented by [Chemical Formula 1].

[Chemical Formula 1]

wherein X and Y are the same or different, and each is independently selected from H, $-SO_3^-$ and $-SO_3H$;

$R_1$ and $R_2$ are the same or different, and each is selected from $C_{1-7}$ alkyl, $C_{8-18}$ alkyl, $-(CH_2)_mSO_3^-$, $-(CH_2)_mSO_3H$, and $R_3$ and $R_4$ are the same or different, and each is selected from $C_{1-7}$ alkyl, $-(CH_2)_mCOOZ_1$ and with the proviso that both of $R_3$ and $R_4$ cannot represent any one selected from $-(CH_2)_mCOOZ_1$ and at the same time;

$Z_1$ and $Z_2$ are the same or different, and each is independently substituted with a substituent selected from H, N-succinimidyl, hydrazinyl, N-hydroxysuccinimidyl, N-hydrosuccinimidyloxy, sulfosuccinimidyloxy, 4-sulfo-2,3,4,5-tetrafluorophenyl, maleinimide$C_{0-10}$alkylaminyl, vinylsulfonyl, vinylsulfonyl$C_{0-6}$alkylaminyl and amino $C_{0-6}$alkyl;

n is an integer of 1-6;
m is an integer of 1-7;
p is an integer of 1-10;
q is an integer of 0-6;
r is an integer of 1-10;
m' is an integer of 1-7;
p' is an integer of 1-10;
q' is an integer of 1-10; and
r' is an integer of 1-10.

According to an embodiment, at least one of $R_1$ and $R_2$ may be

According to another embodiment, at least one of $R_3$ and $R_4$ may be any one selected from $(CH_2)_mCOOZ_1$ and According to still another embodiment of the compound represented by [Chemical Formula 1], $R_1$ and $R_2$ are the same or different, and each is selected from $C_{1-7}$ alkyl, $C_{8-18}$ alkyl, $-(CH_2)_mSO_3^-$, $-(CH_2)_mSO_3H$, and $R_3$ and $R_4$ are the same or different, and each is selected from $C_{1-7}$ alkyl, $-(CH_2)_m COOZ_1$ and

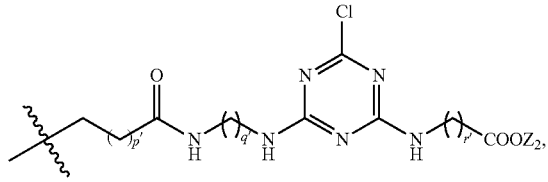

with the proviso that both of $R_3$ and $R_4$ cannot represent any one selected from $-(CH_2)_m COOZ_1$ and

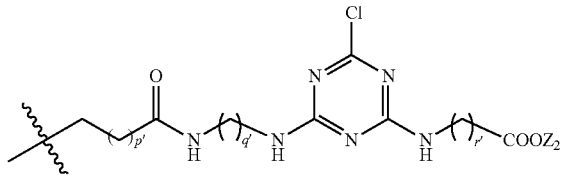

at the same time;

$Z_1$ and $Z_2$ are the same or different, and each independently represents H or N-succinimidyl;

n is an integer of 1-6;

m is an integer of 1-6;

p is an integer of 3-7;

q is an integer of 0-4;

r is an integer of 1-6;

m' is an integer of 1-7;

p' is an integer of 1-10;

q' is an integer of 1-10; and r' is an integer of 1-10.

According to still another embodiment of the compound represented by [Chemical Formula 1], at least one of $R_1$ and $R_2$ represents

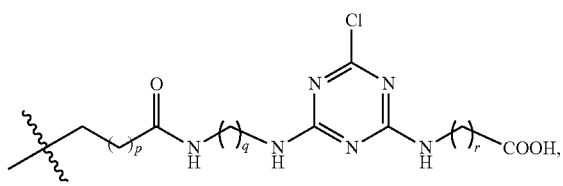

and at least one of $R_3$ and $R_4$ represents $-(CH_2)_m COOZ_1$ or

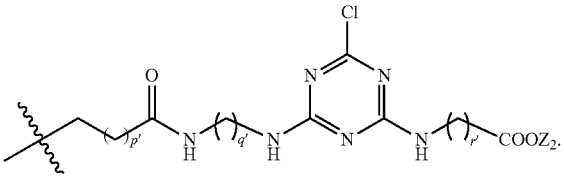

According to still another embodiment, the compound represented by [Chemical Formula 1] may be selected from the following Compound 1-Compound 20, but is not limited thereto.

The compound represented by [Chemical Formula 1] has a structure including two indole compounds linked with each other through an unsaturated hydrocarbon having an intramolecular continuous double bond, and may be designated as CyA depending on the number of carbon atoms (A). However, only Cy3, Cy5 and Cy9 compounds will be exemplified hereinafter, but the scope of the present disclosure is not limited thereto. The method described hereinafter may be used to provide Cy7, Cy11 and Cy13 compounds with ease.

In addition, only the compounds represented by [Chemical Formula 1] wherein q is 0 or 3 will be exemplified hereinafter, but the scope of the present disclosure is not limited thereto. The method described hereinafter may be used to provide the compounds represented by [Chemical Formula 1] wherein q is 1-6.

In addition, only the compounds represented by [Chemical Formula 1] wherein r is 1 or 5 will be exemplified hereinafter, but the scope of the present disclosure is not limited thereto. The method described hereinafter may be used to provide the compounds represented by [Chemical Formula 1] wherein r is 2-10.

In addition, only the compounds represented by [Chemical Formula 1] wherein p is 4, 6 or 9 will be exemplified hereinafter, but the scope of the present disclosure is not limited thereto. The method described hereinafter may be used to provide the compounds represented by [Chemical Formula 1] wherein p is 1-10.

In addition, only the compounds represented by [Chemical Formula 1] wherein q is 3 will be exemplified hereinafter, but the scope of the present disclosure is not limited thereto. The method described hereinafter may be used to provide the compounds represented by [Chemical Formula 1] wherein q is 1-6.

In addition, only the compounds represented by [Chemical Formula 1] wherein r is 5 will be exemplified hereinafter, but the scope of the present disclosure is not limited thereto. The method described hereinafter may be used to provide the compounds represented by [Chemical Formula 1] wherein r is 2-10.

In addition, only the compounds represented by [Chemical Formula 1] wherein p is 5 will be exemplified hereinafter, but the scope of the present disclosure is not limited thereto. The method described hereinafter may be used to provide the compounds represented by [Chemical Formula 1] wherein p is 1-10.

Compound 1

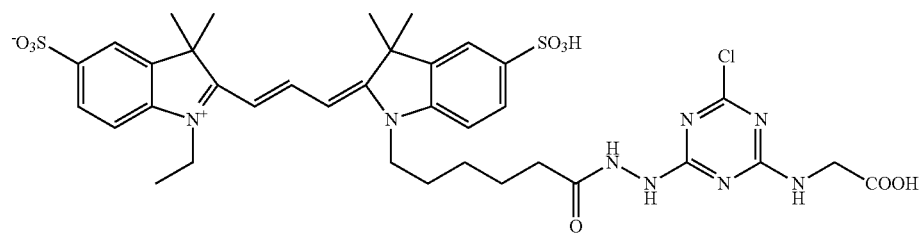

-continued
Compound 2
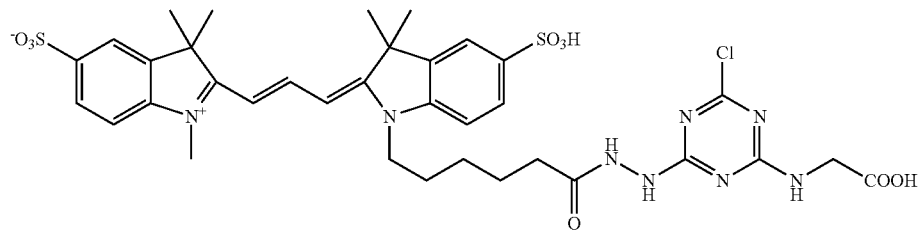
Compound 3
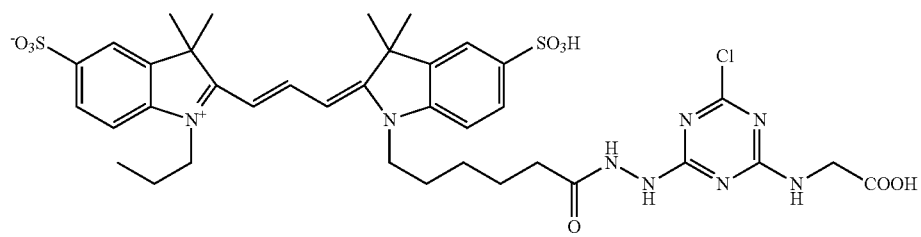
Compound 4
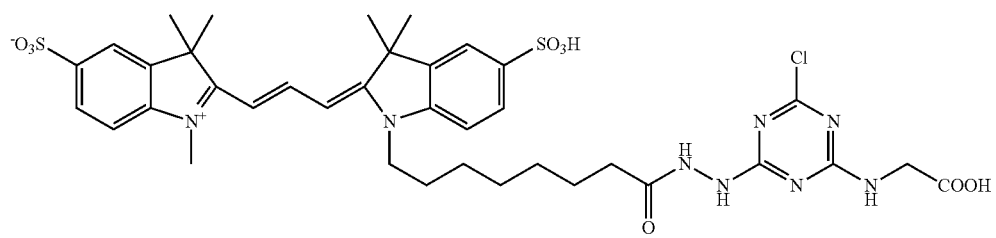
Compound 5
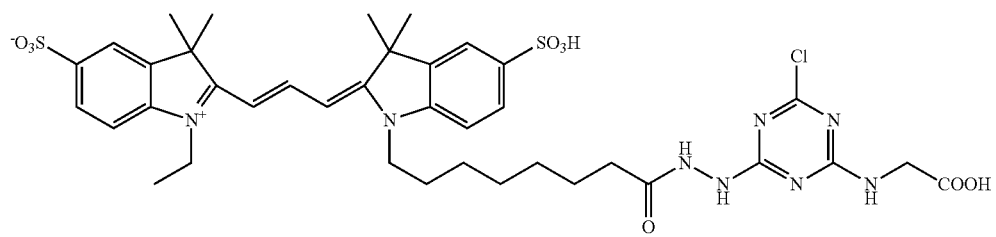
Compound 6
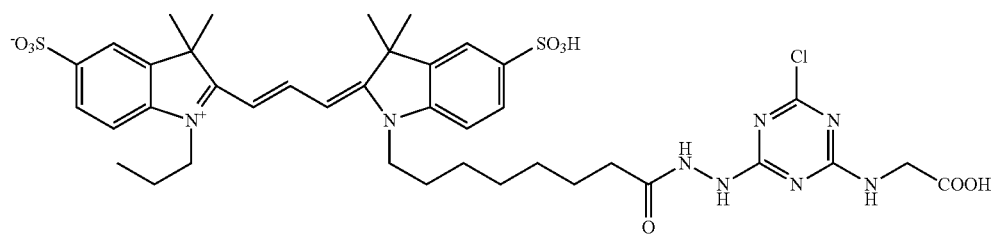
Compound 7
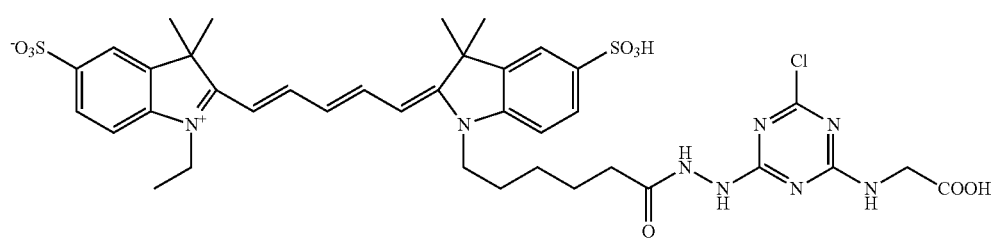

Compound 8
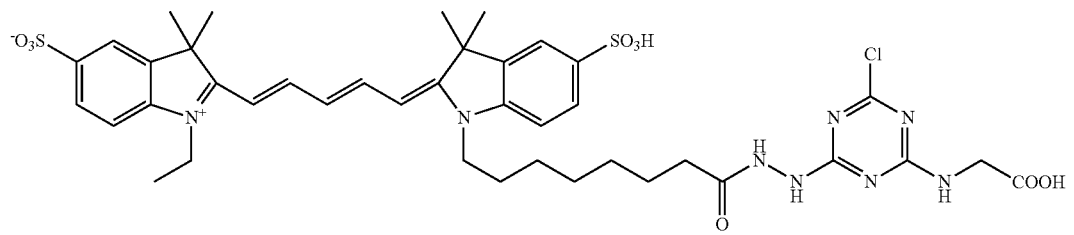
Compound 9
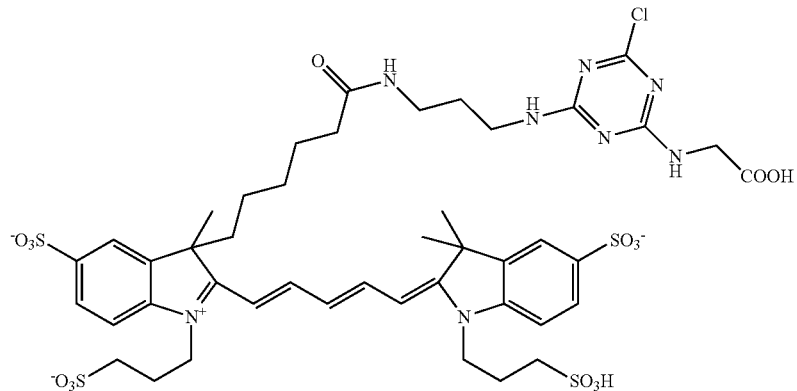
Compound 10
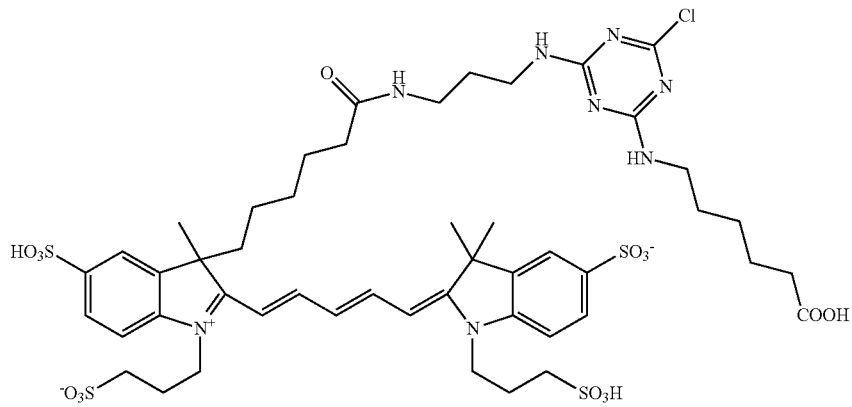
Compound 11
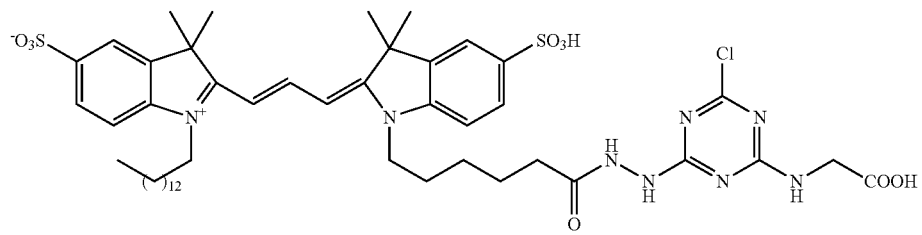
Compound 12
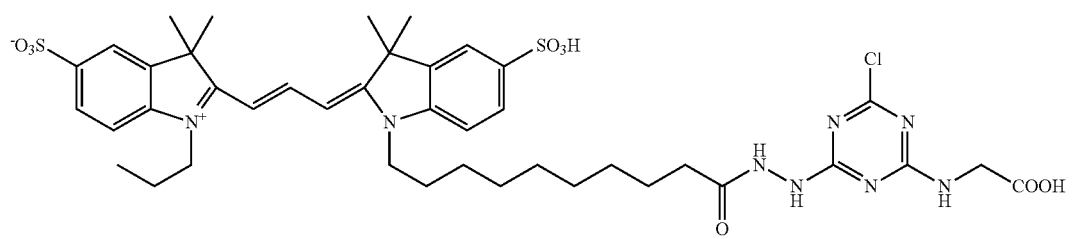

Compound 13
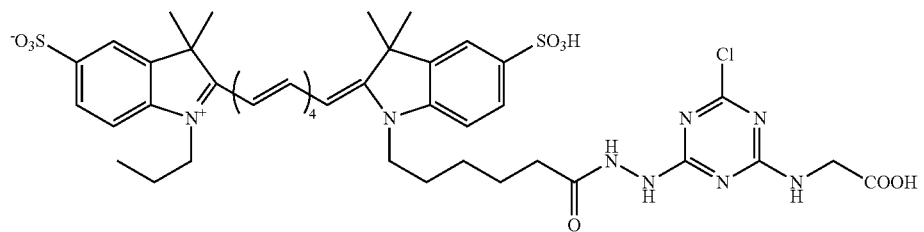
Compound 14
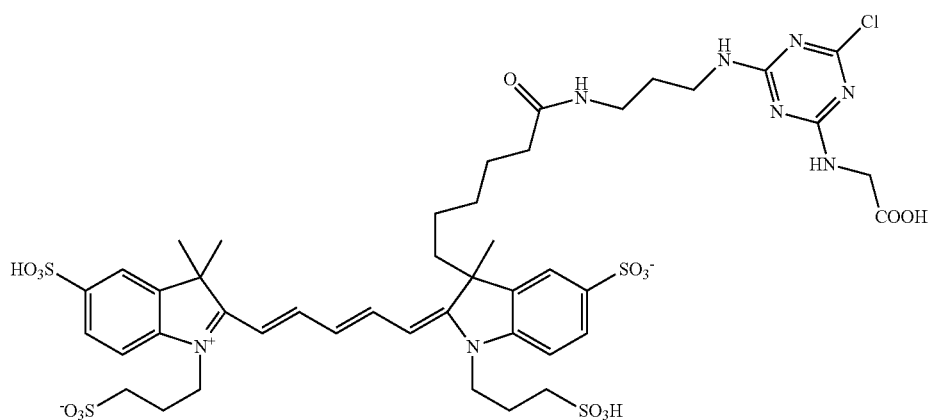
Compound 15
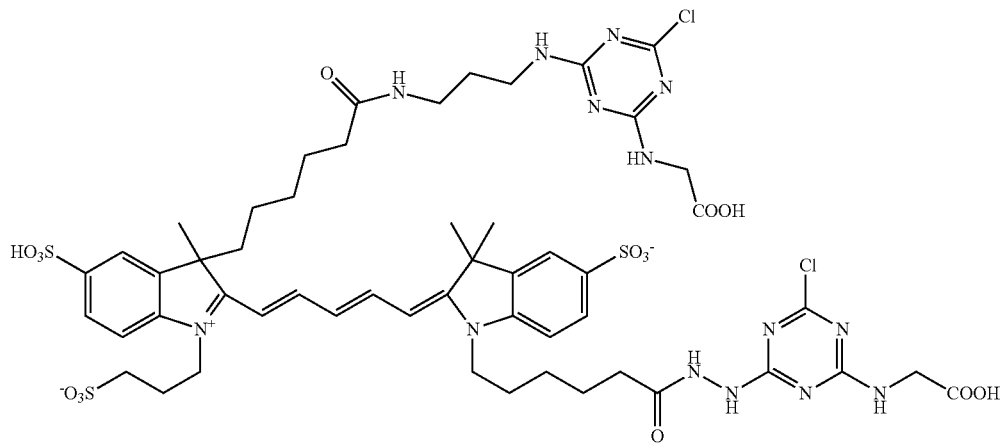
Compound 16
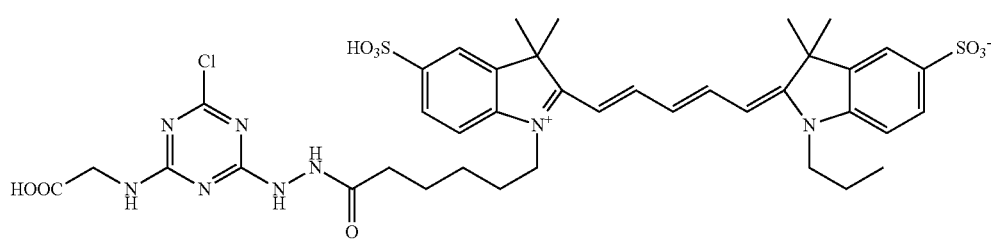

Compound 17
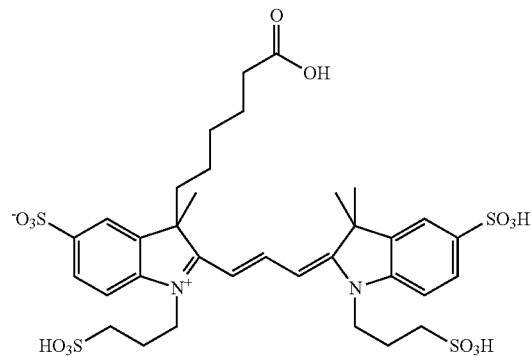
Compound 18
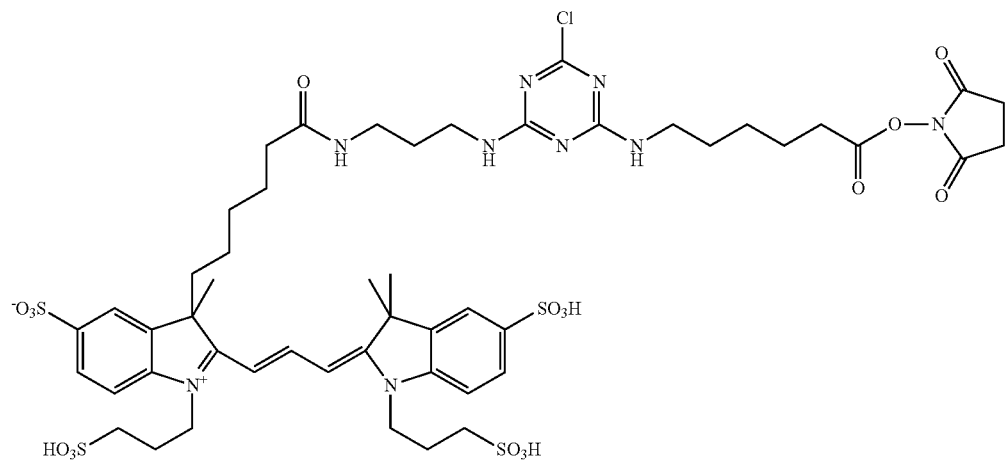
Compound 19
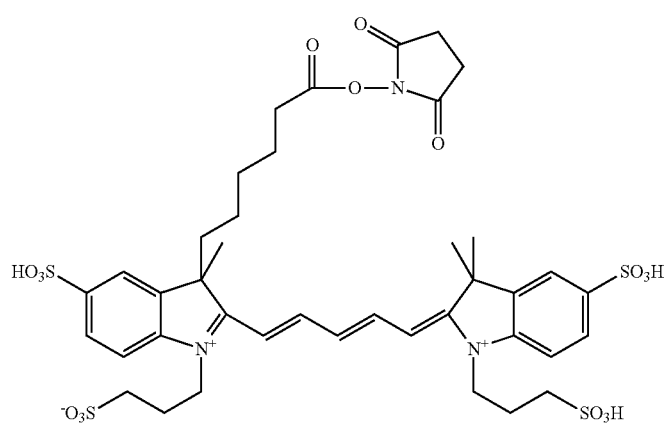

-continued

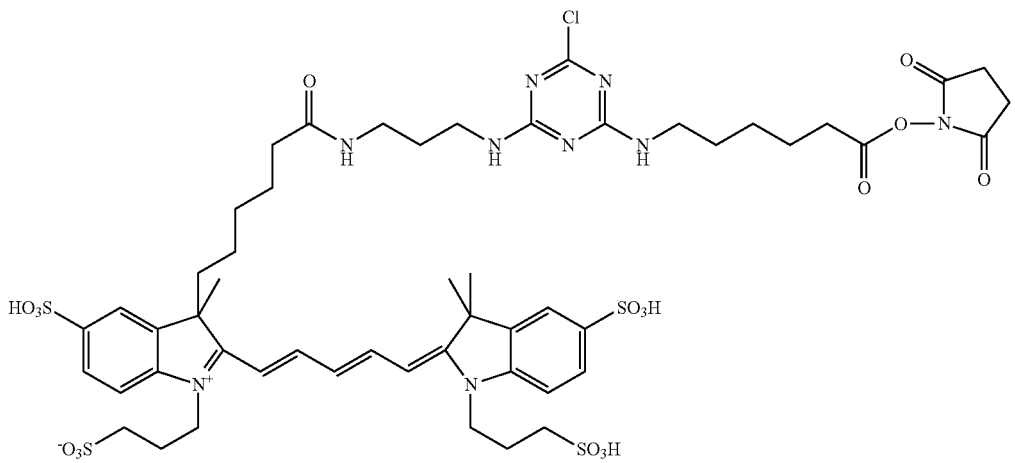

Compound 20

The fluorescent compound represented by [Chemical Formula 1] disclosed herein shows fluorescence with improved intensity even at a lower concentration as compared to the conventional cyanine-based dye compounds.

The fluorescent compound represented by [Chemical Formula 1] disclosed herein absorbs a narrow range of wavelengths of 500-700 nm in the near infrared region, and shows fluorescence with improved intensity at a wavelength of 600-800 nm.

The fluorescent compound represented by [Chemical Formula 1] disclosed herein may be used for labeling a target material, such as a fiber, biomolecule, nanoparticle or an organic compound.

The biomolecule may be selected from the group consisting of proteins, peptides, carbohydrates, sugars, fats, antibodies, proteoglycans, glycoproteins and siRNA, but is not limited thereto.

The target material may be one that is not modified physically or chemically, but is not limited thereto. The target material may be a physically or chemically modified material. Such physical or chemical modification may be made by an experimenter's need. In addition, the target material may be modified so that it may be labeled easily with the fluorescent compound represented by [Chemical Formula 1] disclosed herein.

According to still another embodiment, for the purpose of labeling of a target material, the hydrogen atom of the terminal —COOH in —(CH$_2$)$_m$COOH or

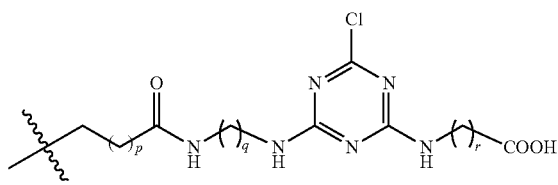

as R$_1$ or R$_2$ defined in the compound represented by [Chemical Formula 1] may be non-substituted or may be modified with a substituent capable of being bound with the functional group present in the structure of a target material within the scope of [Chemical Formula 1]. The substituent capable of being bound with the functional group may be selected from hydrazinyl, N-hydroxysuccinimidyl, N-hydrosuccinimidyloxy, sulfosuccinimidyloxy, 4-sulfo-2,3,4,5-tetrafluorophenyl, maleinimideC$_{0-10}$alkylaminyl, vinyl sulfonyl, vinylsulfonylC$_{0-6}$alkylaminyl and aminoC$_{0-6}$alkyl, but is not limited thereto. When the compound of [Chemical Formula 1] is substituted with the above-mentioned substituents, a target material, such as a fiber, biomolecule, nanoparticle or an organic compound, may be labeled more easily with the compound. The functional group present in the target material may be amine, hydroxyl or thiol group but is not limited thereto.

A method for labeling with the fluorescent compound represented by [Chemical Formula 1] may be carried out by using, as a solvent, a buffer selected from the group consisting of phosphate buffer, carbonate buffer and Tris buffer, an organic solvent selected from the group consisting of dimethyl sulfoxide, dimethyl formamide, methanol, ethanol and acetonitrile, or water, and reacting the compound of [Chemical Formula 1] with a biomolecule, nanoparticle or an organic compound at pH 5-12. The reaction may be carried out at a temperature of 20-80° C. for 30 minutes to 48 hours.

In the case of a biomolecule, most of biomolecules are provided after being dissolved in a buffer in their package units. A separate buffer or pH condition is required frequently to ensure the stability of a biomolecule. Thus, it is not preferred to control a buffer or pH as a variable. The compound of [Chemical Formula 1] disclosed herein easily reacts with various buffers at different reaction temperatures under different pH conditions and emits fluorescence, and thus is suitable for use in labeling of a biomolecule.

In another aspect, there is provided a method for preparing a fluorescent compound represented by [Chemical Formula 1].

The compound represented by the following [Chemical Formula 1] may be prepared from a compound represented by the following [Chemical Formula 2].

[Chemical Formula 2]

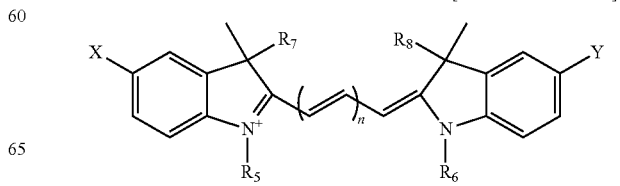

[Chemical Formula 1]

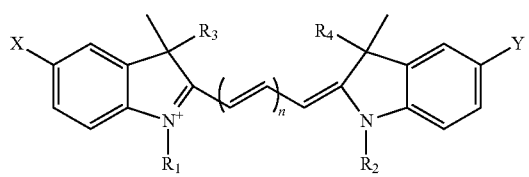

In [Chemical Formula 1] or [Chemical Formula 2], X and Y are the same or different, and each is independently selected from H, $-SO_3^-$ and $-SO_3H$;

$R_1$ and $R_2$ are the same or different, and each is selected from $C_{1-7}$ alkyl, $C_{8-18}$ alkyl, $-(CH_2)_mSO_3^-$, $-(CH_2)_mSO_3H$, and

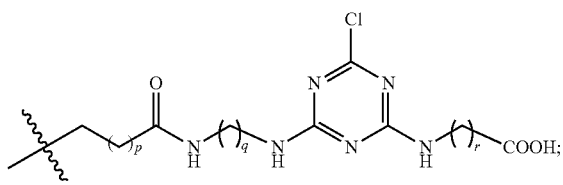

$R_3$ and $R_4$ are the same or different, and each is selected from $C_{1-7}$ alkyl, $-(CH_2)_mCOOZ_1$ and

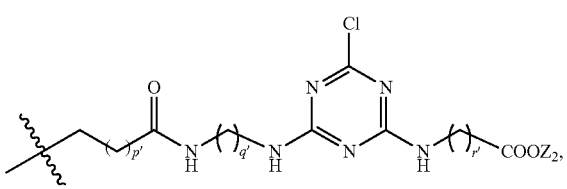

with the proviso that both of $R_3$ and $R_4$ cannot represent any one selected from $-(CH_2)_mCOOZ_1$ and

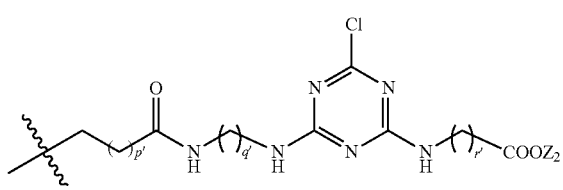

at the same time;

$R_5$ and $R_6$ are the same or different, and each is independently selected from $C_{1-7}$ alkyl, $C_{8-18}$ alkyl, $-(CH_2)_mSO_3^-$, $-(CH_2)_mSO_3H$ and

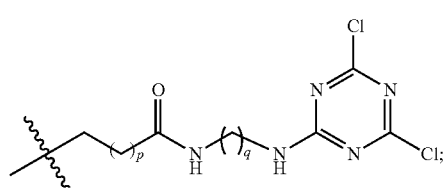

$R_7$ and $R_8$ are the same or different, and each is independently selected from $C_{1-7}$ alkyl, $-(CH_2)_mCOOH$ and

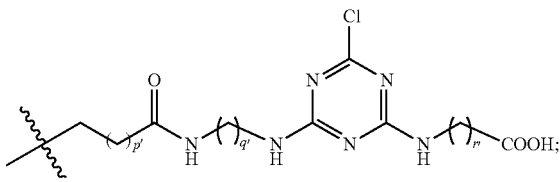

n is an integer of 1-6;
m is an integer of 1-7;
p is an integer of 1-10;
q is an integer of 0-6;
r is an integer of 1-10;
m' is an integer of 1-7;
p' is an integer of 1-10;
q' is an integer of 1-10; and
r' is an integer of 1-10.

According to another embodiment, the reaction may be carried out in an aqueous solution and a base, such as sodium hydrogen carbonate, may be further added to improve the reactivity.

According to still another embodiment, the compound represented by the above [Chemical Formula 2] may be obtained by reacting a compound represented by the following [Chemical Formula 3] with cyanuric chloride.

[Chemical Formula 3]

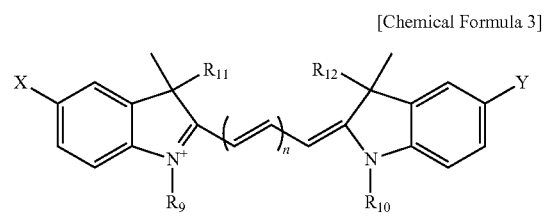

wherein X and Y are the same or different, and each is independently selected from H, $-SO_3^-$ and $-SO_3H$;

$R_9$ and $R_{10}$ are the same or different, and each is independently selected from $C_{1-7}$ alkyl, $C_{8-18}$ alkyl, $-(CH_2)_mSO_3^-$, $-(CH_2)_mSO_3H$ and

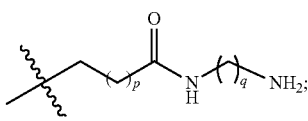

and $R_{11}$ and $R_{12}$ are the same or different, and each is independently selected from $C_{1-7}$ alkyl and

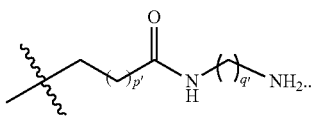

According to still another embodiment, the reaction may be carried out particularly in water or an organic solvent at low temperature, and a base, such as sodium hydrogen carbonate, may be added during the reaction.

According to still another embodiment, the compound represented by [Chemical Formula 3] may be obtained by substituting a compound represented by the following [Chemical Formula 4] with an amine$C_{0-6}$alkylaminyl group.

[Chemical Formula 4]

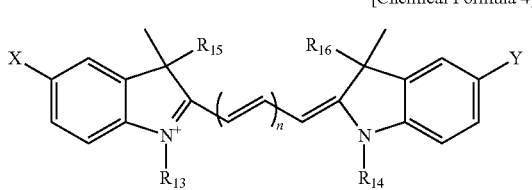

wherein X and Y are the same or different, and each is independently selected from H, —$SO_3^-$ and —$SO_3H$;

$R_{13}$ and $R_{14}$ are the same or different, and each is independently selected from $C_{1-7}$ alkyl, $C_{8-18}$ alkyl, —$(CH_2)_mSO_3^-$, —$(CH_2)_mSO_3H$ and

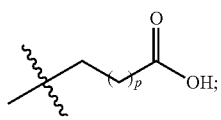

and $R_{15}$ and $R_{16}$ are the same or different, and each is independently selected from $C_{1-7}$ alkyl and

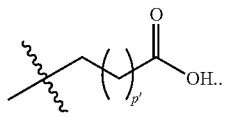

In the amine$C_{0-5}$alkylaminyl group, the amine$C_0$alkylaminyl means hydrazinyl (—$NHNH_2$). It is possible to use a currently used method for substitution with an amine$C_{0-5}$alkylaminyl group.

For example, when introducing a hydrazinyl group, the compound represented by [Chemical Formula 4] may be allowed to react with N,N'-disuccinimidyl carbonate (DSC) added thereto in an organic solvent in the presence of Huenig's base and then with tert-butyl carbazate, and the tert-butoxycarbonyl group may be removed.

Meanwhile, when introducing an amine$C_{0-5}$alkylaminyl, an aminealkylaminyl precursor, one amine of which is protected with a protecting group, such as N,N,N',N'-tetramethyl-O—(N-succinimidyl)uronium tetrafluoroborate, may be used to carry out reaction, but the scope of the present disclosure is not limited thereto.

According to still another embodiment, the compound represented by [Chemical Formula 4] may be obtained by refluxing a compound represented by the following [Chemical Formula 5] with a compound represented by the following [Chemical Formula 6] in the presence of a solvent containing acetic anhydride.

[Chemical Formula 5]

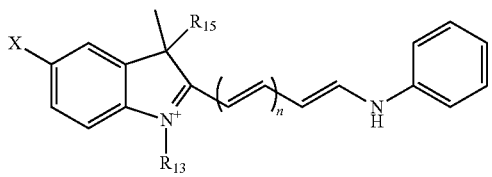

-continued

[Chemical Formula 6]

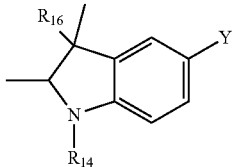

In [Chemical Formula 5] or [Chemical Formula 6], X and Y are the same or different, and each is independently selected from H, —$SO_3^-$ and —$SO_3H$;

$R_{13}$ and $R_{14}$ are the same or different, and each is independently selected from $C_{1-7}$ alkyl, $C_{8-18}$ alkyl, —$(CH_2)_mSO_3^-$, —$(CH_2)_mSO_3H$ and

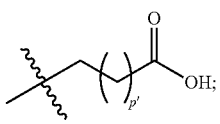

and $R_{15}$ and $R_{16}$ are the same or different, and each is independently selected from $C_{1-7}$ alkyl and

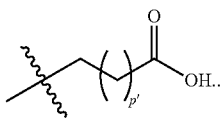

The reaction may be carried out by further adding a base, such as triethylamine, to acetic anhydride and an organic solvent or by further adding pyridine to acetic anhydride in order to improve the reactivity.

In still another aspect, there is provided a contrast medium composition including the fluorescent compound represented by [Chemical Formula 1].

The fluorescent compound represented by [Chemical Formula 1] disclosed herein has a structure including a cyanine chormophore substituted with an alkylcarboxyaminocyanuric chloride, has a narrower wavelength range as compared to the conventional cyanine dyes while showing high fluorescence intensity at low concentration, and causes no cytotoxicity. The fluorescent compound represented by [Chemical Formula 1] disclosed herein effectively absorbs a wavelength in a narrow range of 500-700 nm while showing significantly improved fluorescence intensity in a narrow wavelength range of 600-800 nm. Thus, the compound shows no overlap with the fluorescence region of a biomolecule itself and the composition including the same as an active ingredient may be useful for a contrast medium for in vivo imaging.

In still another aspect, there is provided a method for labeling a compound, which includes binding the fluorescent compound represented by [Chemical Formula 1] with a target material.

According to an embodiment, the target material may be selected from a fiber, biomolecule, nanoparticle and an organic compound, and the biomolecule may be selected from the group consisting of protein, peptides, carbohydrate, sugar, fat, antibodies, proteoglycan, glycoprotein and siRNA.

The compound represented by [Chemical Formula 1] disclosed herein may be used for dyeing proteins with ease through the reaction of proteins with the compound represented by [Chemical Formula 1].

Thus, the labeling may be carried out by using, as a solvent, a buffer selected from the group consisting of phosphate buffer, carbonate buffer and Tris buffer, an organic solvent selected from the group consisting of dimethyl sulfoxide, dimethylformamide, methanol, ethanol and acetonitrile, or water, and by allowing the compound represented by [Chemical Formula 1] with the biomolecule, nanoparticle or organic compound under pH 5-12. The reaction may be carried out sufficiently at a temperature of 20-80° C. for 30 minutes to 48 hours.

Meanwhile, in the case of biomolecules, most of biomolecules are provided after being dissolved in a buffer in their package units. A separate buffer or pH condition is required frequently to ensure the stability of a biomolecule. Thus, it is not preferred to control a buffer or pH as a variable.

The compound of [Chemical Formula 1] disclosed herein has high stability under an aqueous condition and is stored with ease for a long time, and easily reacts with various buffers at different reaction temperatures under different pH conditions and emits fluorescence, and thus is suitable for use in labeling of a biomolecule.

The examples and experiments will now be described. The following examples and experiments are for illustrative purposes only and not intended to limit the scope of this disclosure.

EXAMPLES

To carry out analysis of synthesized compounds, Fourier transform nuclear magnetic resonance (FT-NMR) spectrometry is performed by using Avance 300 or 500 available from Bruker, and liquid chromatography/mass spectrometry (LC/MS) is performed by using LC/MSD (G-1956B) available from Agilent.

The absorption wavelength and absorbance at the maximum wavelength of a synthesized dye are determined by using Cary 8454 UV-VIS available from Agilent, and the emission wavelength and emission at the maximum emission wavelength are determined by using LS-55 available from Perkin Elmer.

Column chromatography for the purpose of isolation and purification of a compound is carried out by using Kieselgel 60 (230-400 mesh) available from Merck as silica gel in the case of normal phase chromatography, and thin layer chromatography (TLC) is carried out by using a glass plate coated with Silica gel 60 GF254 (0.25 mm, Merck). Determination of a compound on TLC is performed by UV rays with a wavelength of 254-365 nm or by using 20-30% ethanol solution of phosphomolybdic acid (PMA) as a color developer or $KMnO_4$ color developer. In the case of reverse phase chromatography, TLC is carried out by using a glass plate coated with Silica gel 60 RP-18 F254S (0.25 mm, Merck) and column chromatography is performed by using Fraction Collector R-660, a medium pressure liquid chromatography system available from Buchi, equipped with a reverse phase column, Lichroprep RP-18 (40-63 m, available from Merck).

Preparation Example 1

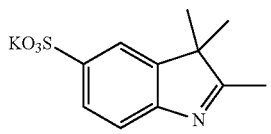

Step 1:
To p-hydrazinobenzenesulfonic acid (10 g, 53 mmol, 1 eq, Aldrich) and 3-methyl-2-butanone (17.18 mL, 160 mmol, 3.02 eq, TCI), 30 mL of acetic acid is added. Next, the reaction mixture is allowed to react by heating under reflux for 4 hours. After cooling the reaction mixture to room temperature, the resultant solid particles are filtered. Then, the resultant product is washed with ethyl acetate three times and dried under reduced pressure (11.34 g, 89%).
Rf=0.68 (RP-C18, acetonitrile/water 1:4 v/v)

Step 2:
Potassium hydroxide (1.427 g, 25.4 mmol, 1.2 eq) is dissolved into 35 mL of propanol and the compound (5.073 g, 21.2 mmol, 1 eq) dissolved in 35 mL of methanol is added thereto. Next, the reaction mixture is agitated at room temperature for 24 hours and filtered to obtain the target compound (5.35 g, 90%).
Rf=0.68 (RP-C18, acetonitrile/water 1:4 v/v)
$^1$H NMR (300 MHz, $D_2O$): δ 7.60 (s, 1H), 7.58 (d, 1H, J=8.32 Hz), 7.32 (d, 1H, J=7.99 Hz), 2.08 (s, 3H), 1.06 (s, 6H)

Preparation Example 2

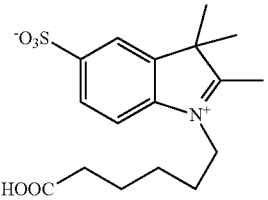

The compound (2.774 g, 10 mmol. 1 eq) of Preparation Example 1 and 6-bromo-n-hexanoic acid (2.34 g, 12 mmol, 1.2 eq, Aldrich) are dissolved into 15 mL of 1,2-dichlorobenzene. Next, the resultant mixture is cooled to room temperature, the solvent is removed therefrom and isopropyl alcohol is added thereto. Then, the reaction mixture is filtered and dried under reduced pressure to obtain the target compound (2.653 g, 75%).
Rf=0.08 (RP-C18, acetonitrile/water 1:4 v/v)
$^1$H NMR (400 MHz, $D_2O$): δ 8.00 (s, 1H), 7.90 (d, 1H, J=8.86 Hz), 7.77 (d, 1H, J=8.43 Hz), 4.37 (t, 2H, J=7.46 Hz), 2.25 (t, 2H, J=7.01 Hz), 1.85 (m, 2H), 1.57-1.26 (m, 13H)
LC/MS, calculated $C_{17}H_{23}NO_5S$ 353.43, found 354.18.

Preparation Example 3

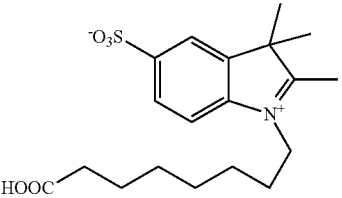

The compound of Preparation Example 1 (1.66 g, 6 mmol, 1 eq) and 8-bromo-octanoic acid (1.34 g, 6 mmol, 1 eq, Aldrich) are heated under reflux with 30 mL 1,2-dichlorobenzene for 12 hours. After cooling the reaction mixture to room temperature, the solvent is removed and isopropyl alcohol is added. Then, the reaction mixture is filtered and dried under reduced pressure to obtain the target compound (1.85 g, 81%).
Rf=0.20 (RP-C18, acetonitrile/water 1:3 v/v)

Example 1

Preparation of Compound 1

Example 1.1

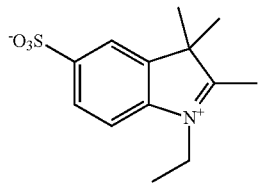

To the compound of Preparation Example 1 (20 g, 72.1 mmol, 1 eq), ethyl iodide (110 mL, 1.375 mmol, 19 eq, TCI) is added. Next, the reaction mixture is heated under reflux. After cooling the reaction mixture to room temperature, the residual ethyl iodide is removed and the resultant product is washed with 50 mL of acetone three times, filtered and dried at 40° C. under reduced pressure to obtain the target compound (18.37 g, 95%).

Rf=0.18 (RP-C18, acetonitrile/water 1:4 v/v)
$^1$H NMR (400 MHz, D$_2$O): δ 7.99 (s, 1H), 7.88 (d, 1H, J=8.23 Hz), 7.80 (d, 1H, J=8.46 Hz), 4.43 (m, 2H), 1.52-1.40 (m, 12H)
LC/MS, calculated C$_{13}$H$_{17}$NO$_3$S 267.34, found 268.16.

Example 1.2

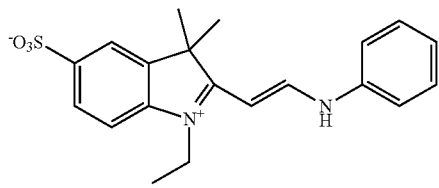

The compound of Example 1.1 (16 g, 59.8 mmol, 1 eq) and N,N'-diphenylformamide (13.2 g, 67.3 mmol, 1.125 eq, TCI) are introduced to a mixed solution of 40 mL of acetic acid with 40 mL of acetic anhydride and the reaction mixture is heated under reflux for 4 hours. After the completion of the reaction, the reaction mixture is cooled to room temperature and the solvent is removed. Then, ethyl acetate is added thereto to form solid. After that, the reaction mixture is filtered and dried under reduced pressure to obtain the target compound (12.97 g, 57%).

Rf=0.25 (RP-C18, acetonitrile/water 1:4 v/v)
$^1$H NMR (300 MHz, DMSO-d$_6$): δ 7.85 (s, 1H), 7.70 (dd, 1H, J=1.35 Hz, 1.32 Hz), 7.53-7.45 (m, 7H), 7.29 (dd, 1H, J=1.92 Hz, 6.66 Hz), 4.13 (m, 2H), 1.70 (s, 6H), 1.32 (t, 3H, J=7.05 Hz)
LC/MS, calculated C$_{20}$H$_{22}$N$_2$O$_3$S 370.47, found 370.98.

Example 1.3

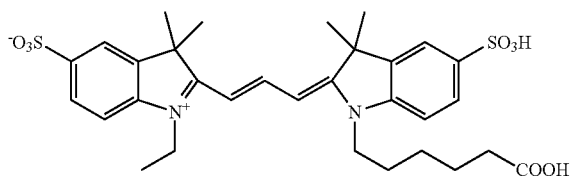

The compound of Example 1.2 (1.01 g, 2.429 mmol, 1 eq) and the compound of Preparation Example 2 (0.86 g, 2.429 mmol, 1 eq) are introduced to a mixed solution of 5 mL of acetic anhydride with 5 mL of pyridine and reaction is carried out at 110° C. for 4 hours. After the completion of the reaction, the reaction mixture is cooled to room temperature and ethyl acetate is added thereto to carry out crystallization. Then, the reaction mixture is filtered and dried under reduced pressure. After that, 15% aqueous acetonitrile solution is used as an eluent for RP-C18 reverse phase chromatography to carry out purification, thereby providing the target compound (0.37 g, 24%).

Rf=0.70 (RP-C18, acetonitrile/water 3:7 v/v)
$^1$H NMR (300 MHz, D$_2$O): δ 8.38 (t, 1H, J=13.5 Hz), 7.78 (s, 2H), 7.73 (t, 2H, J=7.42 Hz), 7.23 (dd, 2H, J=5.25 Hz, 7.97 Hz), 6.24 (dd, 2H, J=4.79 Hz, 4.56 Hz), 3.97 (m, 4H), 2.23 (t, 2H, J=7.26 Hz), 1.73-1.20 (m, 21H)
LC/MS, calculated C$_{31}$H$_{38}$N$_2$O$_8$S$_2$ 630.77, found 631.31.
$\lambda_{abs}$ (water): 549 nm, $\lambda_{fl}$ (water): 573 nm

Example 1.4

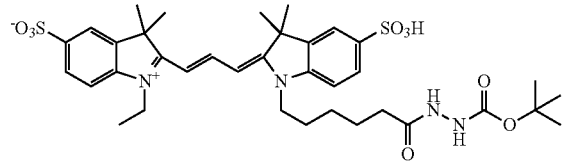

The compound of Example 1.3 (963 mg, 1.53 mmol, 1 eq) is dissolved into 80 mL of dimethyl formamide (DMF) and the mixture is warmed to 40° C. Next, 2.7 mL of Huenig's base is added thereto and DSC (1.17 g, 4.58 mmol, 3 eq, Aldrich) is introduced to the reaction mixture. After agitating the mixture for 1 hour, ethyl acetate is added thereto to obtain a reddish brown solid, which, in turn, is washed with ethyl acetate and ether many times and then filtered. The washed solid is dissolved into 70 mL of DMF, tert-butyl carbazate (303 mg, 2.29 mmol, 1.5 eq, TCI) is introduced thereto, 2.7 mL of Huenig's base is added thereto, and then the resultant mixture is agitated for 12 hours. After the completion of the reaction, ethyl acetate is added thereto to obtain a reddish brown solid, which, in turn is filtered and dried under reduced pressure. Then, 15% aqueous acetonitrile solution is used as an eluent for RP-C18 reverse phase chromatography to carry out purification, thereby providing the target compound (407 mg, 35.8%).

Rf=0.65 (Silica gel, isobutanol/n-propanol/ethyl acetate/water 2:4:1:3 v/v/v/v)

Example 1.5

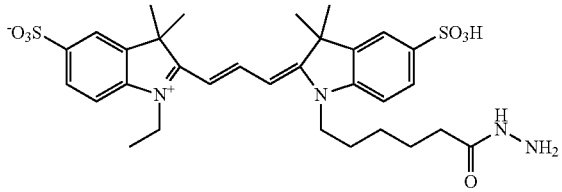

To the compound of Example 1.4 (400 mg, 0.54 mmol, 1 eq), 5 mL of chloroform, 12 mL of TFA and 5 mL of water are introduced. The reaction mixture is agitated at room temperature for 12 hours and subjected to distillation under reduced pressure to obtain a reddish brown solid. Then, 15% aqueous acetonitrile solution is used as an eluent for RP-C18 reverse phase chromatography to carry out purification, thereby providing the target compound (130 mg, 37.3%).

Rf=0.55 (Silica gel, isobutanol/n-propanol/ethyl acetate/water 2:4:1:3 v/v/v/v)

Example 1.6

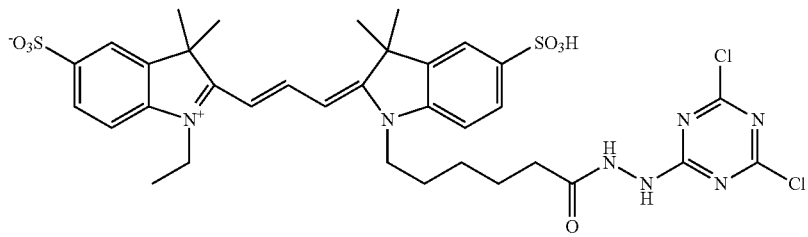

Cyanuric chloride (17 mg, 0.093 mmol, 1 eq, Aldrich) is introduced to 10 mL of water and the mixture is cooled to 0° C., followed by agitation for 30 minutes. The compound of Example 1.5 (60 mg, 0.093 mmol, 1 eq) is added thereto while maintaining the temperature, followed by agitation for 10 minutes. Next, 15 mg of sodium hydrogen carbonate is added to the reaction mixture and reaction is carried out for 2 hours while maintaining the temperature at 0° C. Then, 15% aqueous acetonitrile solution is used as an eluent for RP-C18 reverse phase chromatography to carry out purification, thereby providing the target compound (34 mg, 46.1%).

Rf=0.6 (Silica gel, isobutanol/n-propanol/ethyl acetate/water 2:4:1:3 v/v/v/v)

Example 1.7

Synthesis of Compound 1

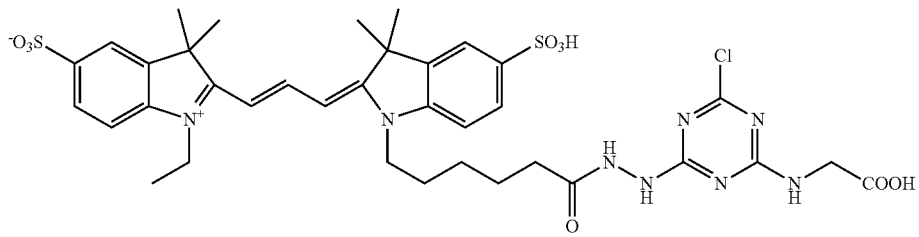

The compound of Example 1.6 (50 mg, 0.063 mmol, 1 eq) is dissolved completely into 3 mL of water, glycine (14 mg, 0.189 mmol, 3 eq) is added thereto and the reaction mixture is agitated for 10 minutes. Next, 15 mg of sodium hydrogen carbonate is added thereto and the reaction mixture is agitated for 12 hours. Then, 15% aqueous acetonitrile solution is used as an eluent for RP-C18 reverse phase chromatography to carry out purification, thereby providing the target compound, Compound 1 (32 mg, 61%).

Rf=0.5 (Silica gel, acetonitrile/water 9:1 v/v)

MALDI-TOF M/S, calculated $C_{36}H_{43}ClN_8O_9S_2$ 831.36, found 831.12.

Hereinafter, unless otherwise stated in the following Examples 2-10, the target compounds are obtained in the same manner as Example 1 or in a similar way.

Example 2

Preparation of Compound 2

Example 2.1

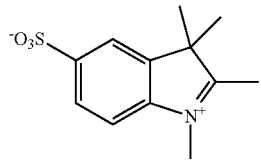

The target compound is obtained in the same manner as Example 1.1, except that methyl iodide is used in combination with the compound of Preparation Example 1 (13.45 g, 82%).

Rf=0.13 (RP-C18, acetonitrile/water 1:4 v/v)

Example 2.2

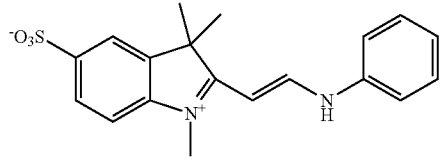

The target compound is obtained in the same manner as Example 1.2, except that the compound of Example 2.1 is used instead of the compound of Example 1.1 (6.48 g, 52%).

Rf=0.33 (RP-C18, acetonitrile/water 1:4 v/v)

Example 2.3

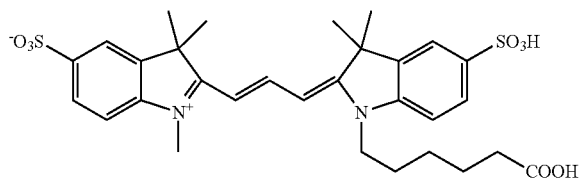

(0.94 g, 27%)
Rf=0.80 (RP-C18, acetonitrile/water 3:7 v/v)
$^1$H NMR (300 MHz, D$_2$O): δ 7.95 (m, 1H), 7.84-7.62 (m, 4H), 7.46 (d, 2H, J=7.89 Hz), 6.51 (d, 2H, J=8.22 Hz), 4.41 (t, 2H, J=8.07 Hz), 3.56 (s, 3H), 1.90 (m, 2H), 1.70-1.24 (m, 18H)
MALDI-TOF M/S, calculated C$_{30}$H$_{36}$N$_2$O$_8$S$_2$ 616.75, found 617.53.
$λ_{abs}$ (water): 546 nm, $λ_{fl}$ (water): 570 nm Example 2.4

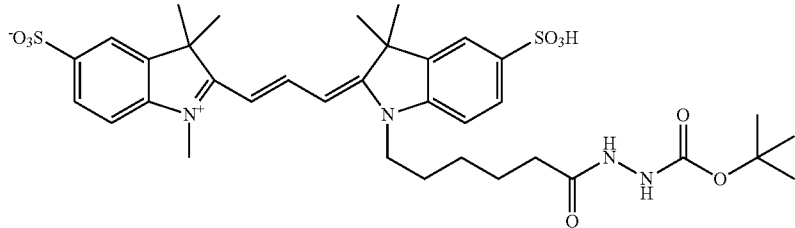

(820 mg, 51.9%)
Rf=0.7 (Silica gel, isobutanol/n-propanol/ethyl acetate/water 2:4:1:3 v/v/v/v)

Example 2.5

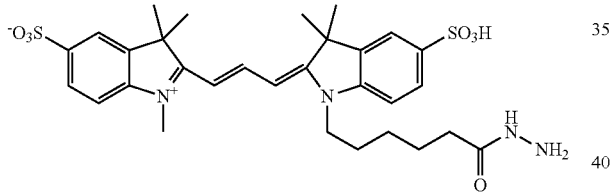

(450 mg, 65.2%)
Rf=0.55 (Silica gel, isobutanol/n-propanol/ethyl acetate/water 2:4:1:3 v/v/v/v)

Example 2.6

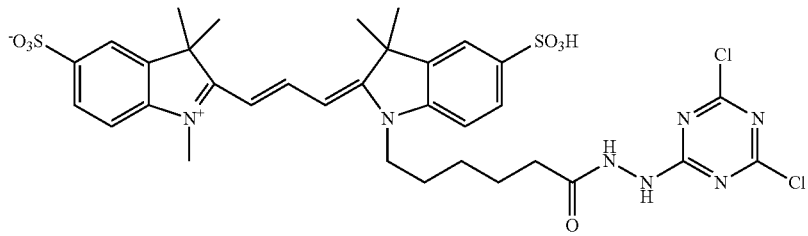

(183 mg, 33.0%)
Rf=0.6 (Silica gel, isobutanol/n-propanol/ethyl acetate/water 2:4:1:3 v/v/v/v)

Example 2.7

Synthesis of Compound 2

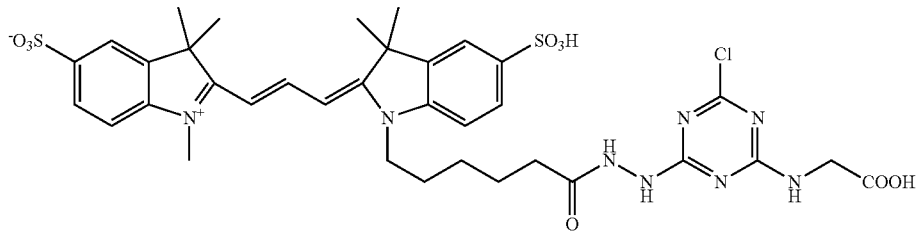

(41 mg, 39.1%)
Rf=0.4 (Silica gel, acetonitrile/water 9:1 v/v)
MALDI-TOF M/S, calculated $C_{35}H_{41}ClN_8O_9S_2$ 817.33, found 817.02.

Example 3

Preparation of Compound 3

Example 3.1

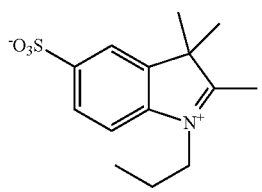

(19.81 g, 98%)
Rf=0.45 (RP-C18, acetonitrile/water 1:4 v/v)

Example 3.2

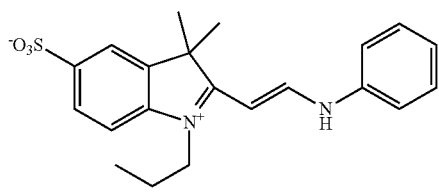

(10.28 g, 85%)
Rf=0.10 (RP-C18, acetonitrile/water 1:4 v/v)

Example 3.3

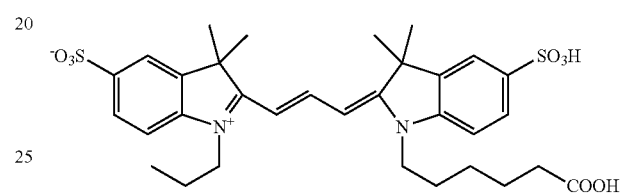

(3.06 g, 20.6%)
Rf=0.49 (RP-C18, acetonitrile/water 3:7 v/v)
$^1$H NMR (300 MHz, DMSO-$d_6$): δ 8.34 (t, 1H, J=13.2 Hz), 7.78 (s, 2H), 7.65 (d, 2H, J=8.04 Hz), 7.39 (m, 2H), 6.56 (dd, 2H, J=13.16 Hz, 13.44 Hz), 4.10 (m, 4H), 1.88 (t, 2H, J=6.88 Hz), 1.77-1.38 (m, 21H), 0.96 (t, 3H, J=7.24 Hz)
LC/MS, calculated $C_{32}H_{40}N_2O_8S_2$ 644.8, found 643.29.
$λ_{abs}$ (water): 550 nm, $λ_{fl}$ (water): 574 nm

Example 3.4

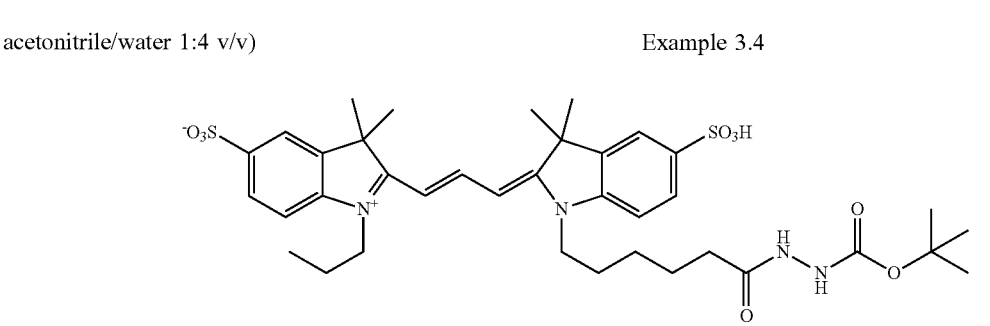

(625 mg, 39.8%)
Rf=0.65 (Silica gel, isobutanol/n-propanol/ethyl acetate/water 2:4:1:3 v/v/v/v)

Example 3.5

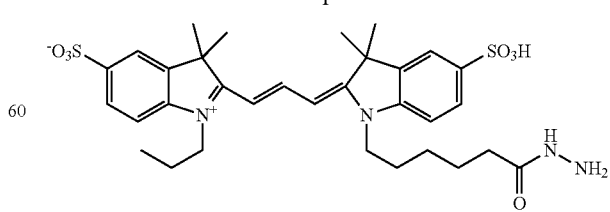

(373 mg, 70.4%)
Rf=0.55 (Silica gel, isobutanol/n-propanol/ethyl acetate/water 2:4:1:3 v/v/v/v)

Example 3.6

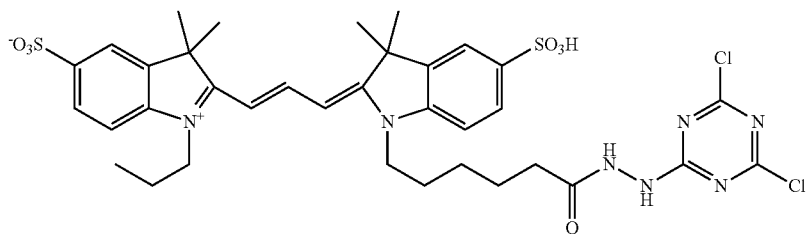

(300 mg, 70.0%)

Rf=0.7 (Silica gel, isobutanol/n-propanol/ethyl acetate/water 2:4:1:3 v/v/v/v)

Example 3.7

Synthesis of Compound 3

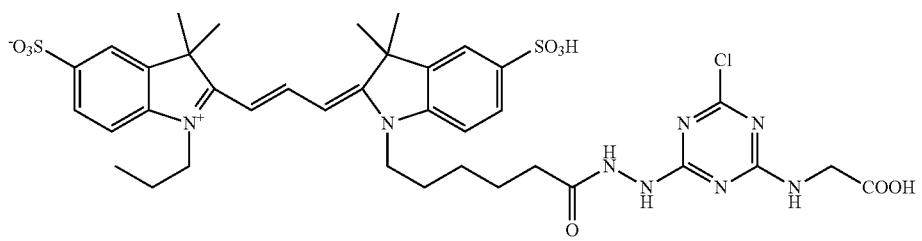

(61 mg, 38.8%)

Rf=0.6 (Silica gel, isobutanol/n-propanol/ethyl acetate/water 2:4:1:3 v/v/v/v)

MALDI-TOF M/S, calculated $C_{37}H_{45}ClN_8O_9S_2$ 845.38, found 845.48.

Example 4

Preparation of Compound 4

Example 4.1

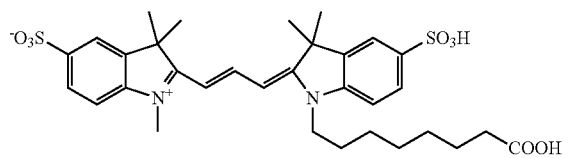

The compound of Example 2.2 and the compound of Preparation Example 3 are used to obtain the target compound in the same manner as Example 1.3 (0.85 g, 22%).

Rf=0.6 (RP-C18, acetonitrile/water 1:3 v/v)

Example 4.2

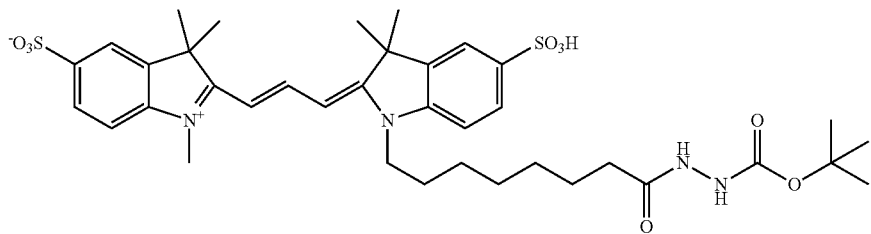

(655 mg, 37.1%)
Rf=0.65 (Silica gel, isobutanol/n-propanol/ethyl acetate/water 2:4:1:3 v/v/v/v)

Example 4.3

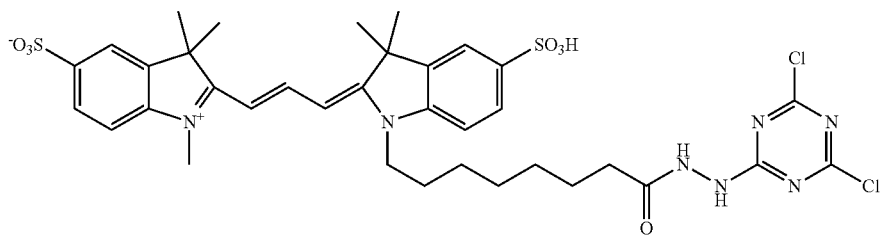

(470 mg, 86.0%)
Rf=0.6 (Silica gel, isobutanol/n-propanol/ethyl acetate/water 2:4:1:3 v/v/v/v)

Example 4.4

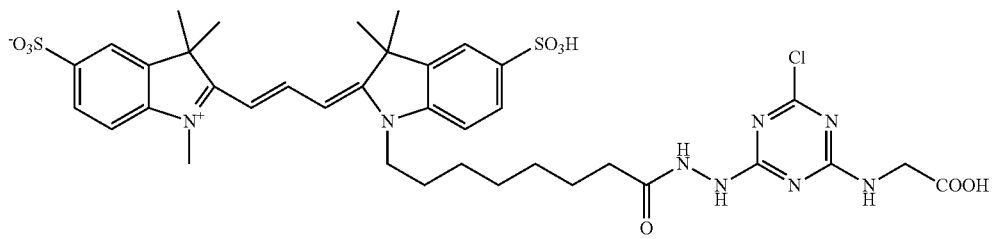

(242 mg, 45.9%)
Rf=0.65 (Silica gel, isobutanol/n-propanol/ethyl acetate/water 2:4:1:3 v/v/v/v)

Example 4.5

(52 mg, 33.1%)
Rf=0.45 (Silica gel, acetonitrile/water 9:1 v/v)
MALDI-TOF M/S, calculated $C_{37}H_{45}ClN_8O_9S_2$ 845.38, found 845.52.

Example 5

Preparation of Compound 5

Example 5.1

(0.31 g, 25%)
Rf=0.6 (RP-C18, acetonitrile/water 1:3 v/v)
LC/MS, calculated $C_{33}H_{42}N_2O_8S_2$ 658.83, found 656.9.

Example 5.2

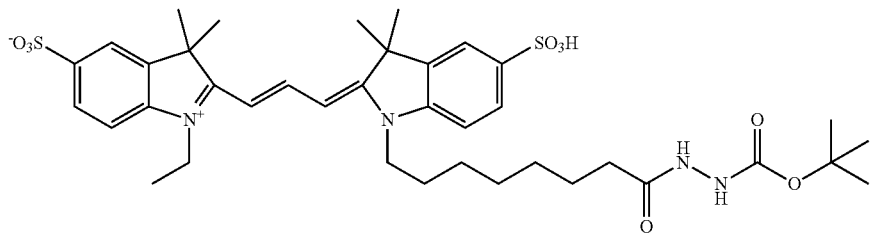

(603 mg, 38.7%)
Rf=0.60 (Silica gel, isobutanol/n-propanol/ethyl acetate/water 2:4:1:3 v/v/v/v)

Example 5.3

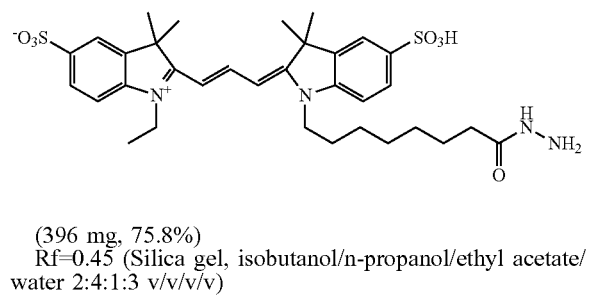

(396 mg, 75.8%)
Rf=0.45 (Silica gel, isobutanol/n-propanol/ethyl acetate/water 2:4:1:3 v/v/v/v)

Example 5.4

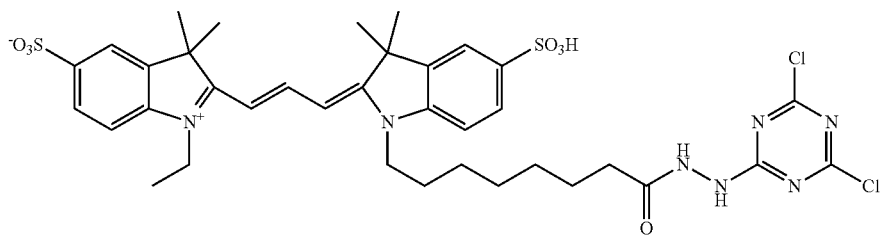

(155 mg, 33.4%)
Rf=0.55 (Silica gel, isobutanol/n-propanol/ethyl acetate/water 2:4:1:3 v/v/v/v)

Example 5.5

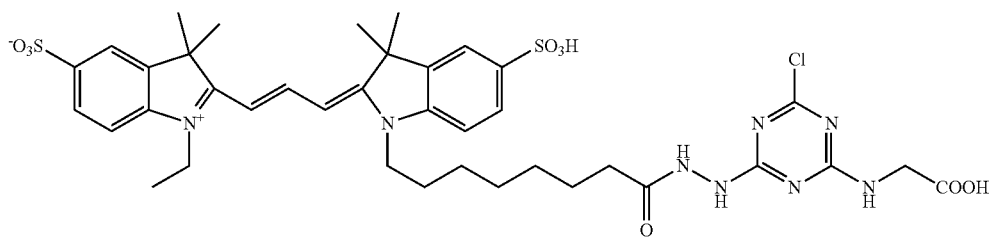

(23 mg, 21.9%)
Rf=0.45 (Silica gel, acetonitrile/water 9:1 v/v)
MALDI-TOF M/S, calculated $C_{38}H_{47}ClN_8O_9S_2$ 859.41, found 859.57.

Example 6

Preparation of Compound 6

Example 6.1

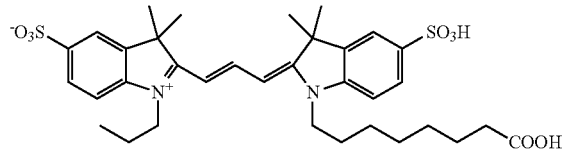

(2.09 g, 31%)
Rf=0.52 (RP-C18, acetonitrile/water 1:3 v/v)
LC/MS, calculated $C_{34}H_{44}N_2O_8S_2$ 672.85, found 671.04.

Example 6.2

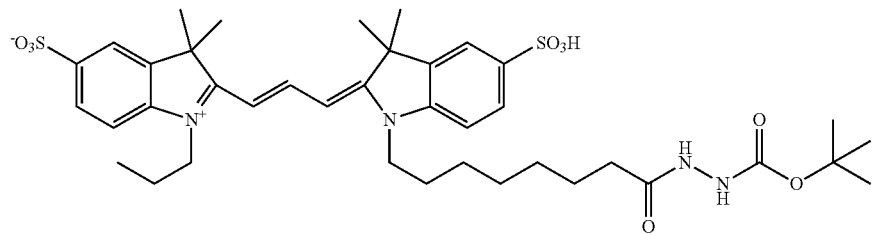

(510 mg, 40.1%)
Rf=0.55 (Silica gel, isobutanol/n-propanol/ethyl acetate/water 2:4:1:3 v/v/v/v)

Example 6.3

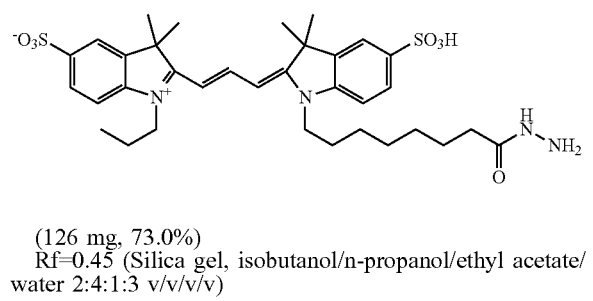

(126 mg, 73.0%)
Rf=0.45 (Silica gel, isobutanol/n-propanol/ethyl acetate/water 2:4:1:3 v/v/v/v)

Example 6.4

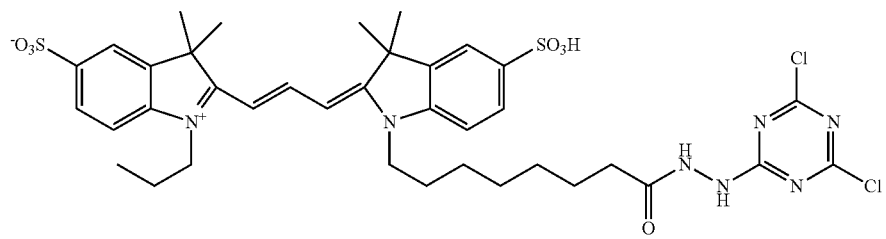

(88 mg, 36.2%)
Rf=0.50 (Silica gel, isobutanol/n-propanol/ethyl acetate/water 2:4:1:3 v/v/v/v)

Example 6.5

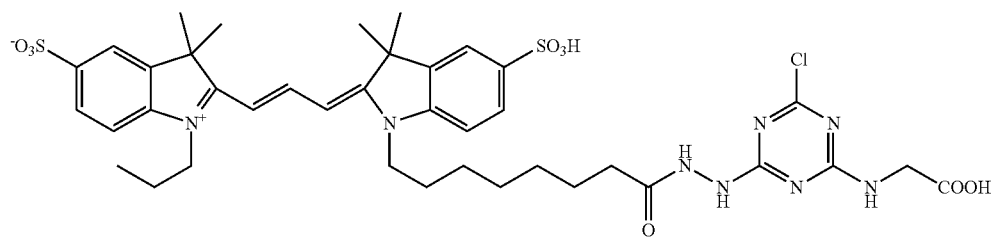

(36 mg, 41.5%)
Rf=0.45 (Silica gel, isobutanol/n-propanol/ethyl acetate/water 2:4:1:3 v/v/v/v)

Example 7

Preparation of Compound 7

Example 7.1

The compound of Example 1.1 (2.2 g, 8.23 mmol, 1 eq) and malonaldehyde dianilide hydrochloride (2.55 g, 9.88 mmol, 1.2 eq, TCI) are introduced to a mixed solution of 10 mL of acetic acid with 10 mL of acetic anhydride and the reaction mixture is heated under reflux for 4 hours. The reaction mixture is cooled to room temperature, the reaction solvent is removed and ethyl acetate is used to form solid, which, in turn, is filtered and dried under reduced pressure to obtain the target compound (3.47 g, 96%).

Rf=0.20 (RP-C18, acetonitrile/water 1:4 v/v).

Example 7.2

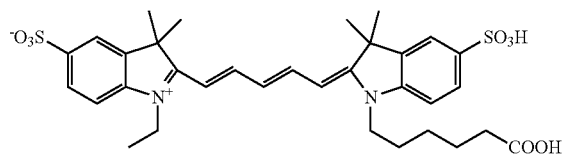

The compound of Example 7.1 (6.40 g, 14.6 mmol. 1 eq) and the compound of Preparation Example 2 (5.12 g, 14.6 mmol. 1 eq) are introduced to 80 mL of pyridine and reaction is carried out at 60° C. for 4 hours. The reaction mixture is cooled to room temperature and ethyl acetate is added thereto to form a blue solid, which, in turn, is filtered and dried under reduced pressure. Then, 25% aqueous acetonitrile solution is used as an eluent for RP-C18 reverse phase chromatography to carry out purification, thereby providing the target compound (2.09 g, 22%).

Rf=0.58 (RP-C18, acetonitrile/water 3:7 v/v)

$^1$H NMR (400 MHz, DMSO-d$_6$): δ 8.34 (t, 2H, J=13.2 Hz), 7.80 (s, 2H), 7.63 (d, 2H, J=8.16 Hz), 7.30 (dd, 2H, J=2.80 Hz, 2.76 Hz), 6.58 (t, 1H, J=12.2 Hz), 6.30 (dd, 2H, J=8.64 Hz, 8.56 Hz), 4.13-4.06 (m, 4H), 1.98 (t, 2H, J=6.84 Hz), 1.72-1.18 (m, 21H)

LC/MS, calculated $C_{33}H_{39}N_2O_8S_2$— 655.22, found 655.24.

$λ_{abs}$ (water): 647 nm, $λ_{fl}$ (water): 678 nm

Example 7.3

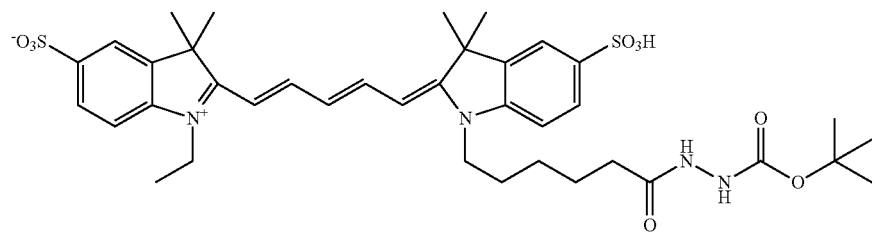

(200 mg, 28.4%)

Rf=0.7 (Silica gel, isobutanol/n-propanol/ethyl acetate/water 2:4:1:3 v/v/v/v)

Example 7.4

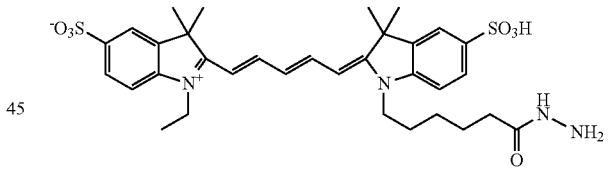

(150 mg, 86%)

Rf=0.56 (Silica gel, acetonitrile/water=12:1 v/v)

Example 7.5

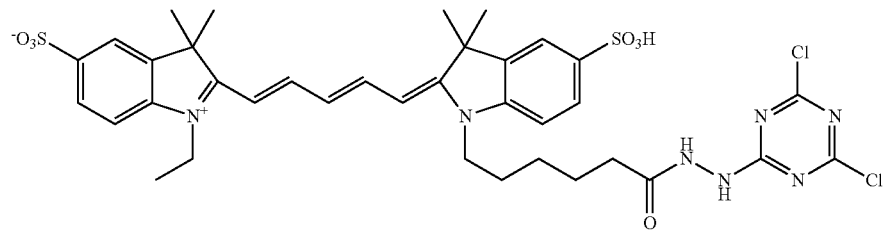

(15 mg, 61.5%)

Rf=0.59 (Silica gel, isobutanol/n-propanol/ethyl acetate/water 2:4:1:3 v/v/v/v)

Example 7.6
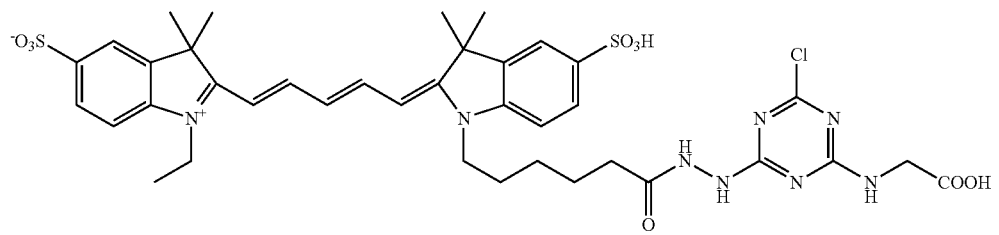
(10 mg, 63.7%)
Rf=0.1 (Silica gel, acetonitrile/water=12:1 v/v)
Example 8
Preparation of Compound 8
Example 8.1
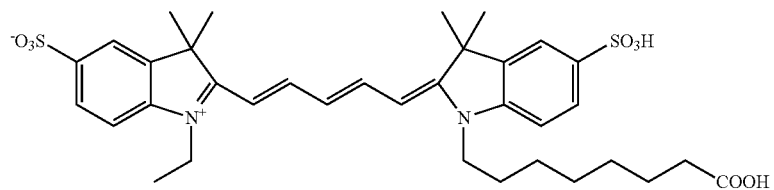
(0.52 g, 6.75%)
Rf=0.55 (Silica gel, isobutanol/n-propanol/ethyl acetate/water 2:4:1:3 v/v/v/v)
Example 8.2
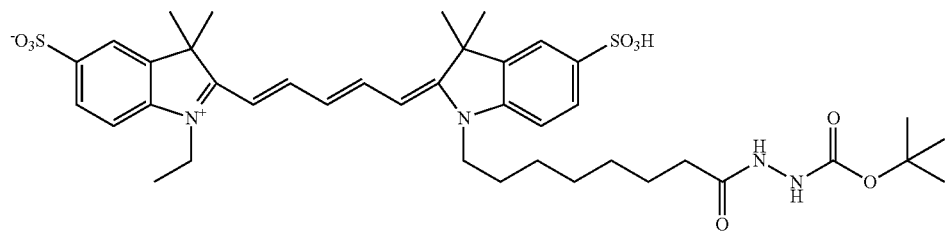
(250 mg, 30.5%)
Rf=0.65 (Silica gel, isobutanol/n-propanol/ethyl acetate/water 2:4:1:3 v/v/v/v)
Example 8.3
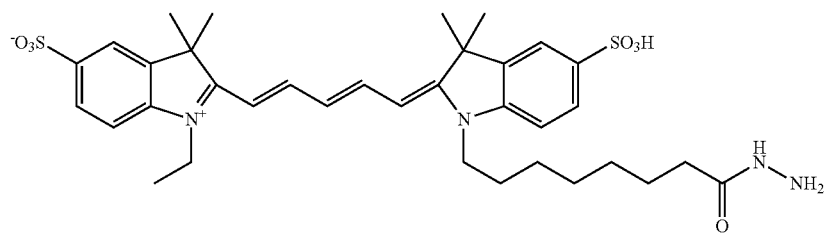
(150 mg, 68.6%)
Rf=0.65 (Silica gel, acetonitrile/water=8:1 v/v)

Example 8.4

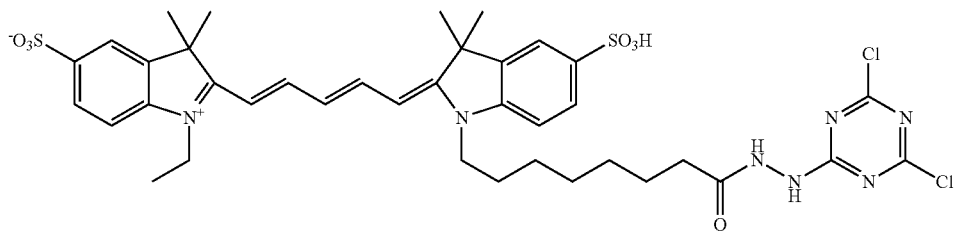

(200 mg, 59.2%)
Rf=0.55 (Silica gel, isobutanol/n-propanol/ethyl acetate/water 2:4:1:3 v/v/v/v)

Example 8.5

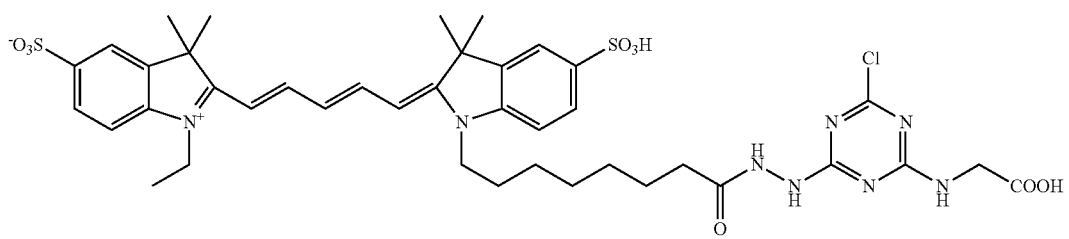

(25 mg, 20.6%)
Rf=0.475 (Silica gel, acetonitrile/water=12:1 v/v)

Example 9

Preparation of Compound 9

Example 9.1

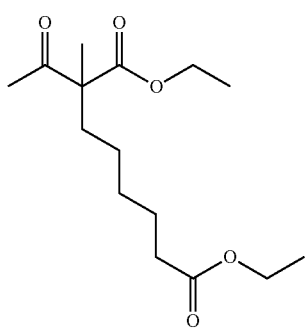 [SMILES: CCOC(=O)CCCCCC(C)(C(C)=O)C(=O)OCC]

Ethyl 2-methyl acetoacetate (29.2 mL, 0.203 mol, 1 eq), 21% sodium ethoride solution (64 mL, 0.816 mol, 4 eq), ethyl 6-bromohexanoate (34 mL, 0.192 mol, 1 eq) and ethanol (200 mL) are added and the mixture is subjected to reflux at 120° C. for 12 hours. Next, the solvent is neutralized with 1M hydrochloric acid and extraction is carried out by using chloroform and distilled water. The extracted solvent is dried under reduced pressure and purification is carried out by normal phase chromatography to obtain the target compound (36.8 g, 63.4%).
Rf=0.34 (Silica gel, hexane/ethyl acetate=10:1 v/v)

Example 9.2

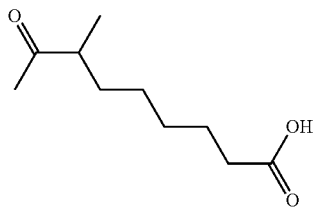

To the compound of Example 9.1 (13.7 g, 0.0486 mol, 1 eq), sodium hydroxide (6.2 g, 0.170 mol, 3.5 eq), methanol (47.2 mL) and distilled water (15.6 mL) are added. Next, the mixture is subjected to reflux at 50° C. for 12 hours. Then, the solvent is dried under reduced pressure and adjusted to pH 1 by using 1M hydrochloric acid. After that, extraction is carried out by using ethyl acetate and the resultant product is dried under reduced pressure to obtain the target compound (8.17 g, 90.7%)
Rf=0.05 (Silica gel, hexane/ethyl acetate=10:1 v/v)

Example 9.3

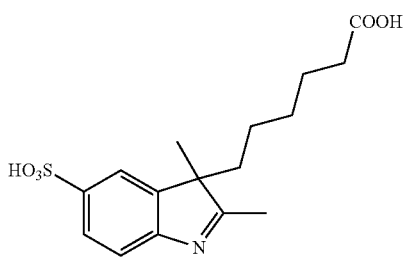 [SMILES: CC1=Nc2ccc(S(=O)(=O)O)cc2C1(C)CCCCCC(=O)O]

To the compound of Example 9.2 (8.165 g, 0.0438 mol, 1 eq), p-hydrazinobenzensulfonic acid hemihydrate (8.25 g, 0.0438 mol, 1 eq) is added. Next, the mixture is subjected to reflux at 120° C. for 5 hours. After the completion of the reaction, the resultant product is dried under reduced pressure and purified by using normal phase chromatography (12.6 g, 84.8 Rf=0.51 (Silica gel, isobutanol/n-propanol/ethyl acetate/water 2:4:1:3 v/v/v/v)

Example 9.4

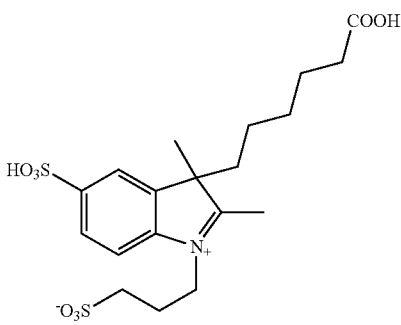

To the compound of Example 9.3 (12.57 g, 0.07 mol, 1 eq), sodium acetate (4.16 g, 0.061 mol, 1.65 eq), 1,3-propane sultone (21.3 mL, 0.243 mol, 6.57 eq) and acetonitrile (24.8 mL) are added. Next, the mixture is subjected to reflux at 110° C. for 5 hours. After the completion of the reaction, the resultant product is dried under reduced pressure and purified by using reverse phase chromatography (12 g, 70.6%)

Rf=0.3 (Silica gel, isobutanol/n-propanol/ethyl acetate/water 2:4:1:3 v/v/v/v)

Example 9.5

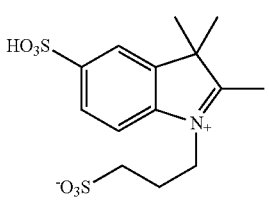

To the compound of Preparation Example 1 (50 g, 0.18 mol, 1 eq), sodium acetate (17.87 g, 0.216 mol, 1.2 eq), 1,3-propane sultone (70.5 mL, 0.8 mol, 4.5 eq) and acetonitrile (42 mL) are added. Next, the mixture is subjected to reflux at 110° C. for 12 hours, crystallized with ethyl acetate, filtered and dried under reduced pressure (61 g, 94%).

Rf=0.3 (Silica gel, isobutanol/n-propanol/ethyl acetate/water 2:4:1:3 v/v/v/v)

Example 9.6

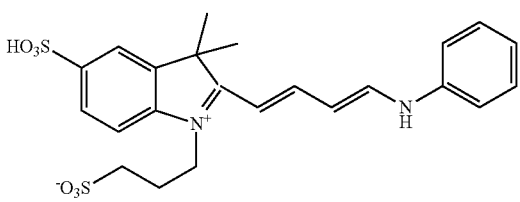

To the compound of Example 9.5 (60 g, 0.166 mol, 1 eq), malonaldehyde dianilide hydrochloride (42.9 g, 0.166 mol, 1 eq), triethylamine (2.3 mL, 0.016 mol, 0.1 eq) and acetic acid (551 mL) are added. Next, the mixture is subjected to reflux at 140° C. After the completion of the reaction, the resultant product is crystallized with ethyl acetate, filtered and dried under reduced pressure, and purified by using normal phase chromatography (7.5 g, 8.5%).

Rf=0.55 (Silica gel, isobutanol/n-propanol/ethyl acetate/water 2:4:1:3 v/v/v/v)

Example 9.7

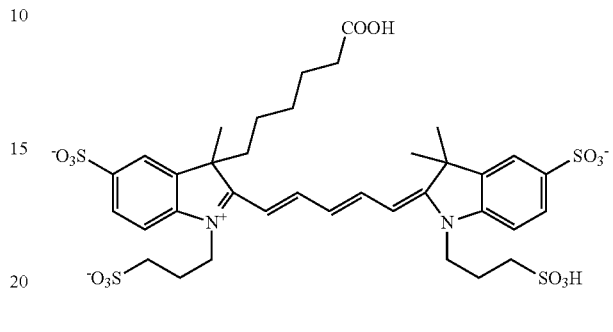

The compound of Example 9.4 (6.5 g, 0.014 mol, 1 eq) and the compound of Example 9.6 (7.5 g, 0.014 mol, 1 eq) are added to a mixed solution of triethylamine (16.6 mL, 0.12 mol, 8.5 eq) with acetic anhydride (7.3 mL) and DMF (75 mL). Next, the mixture is allowed to react at room temperature for 1 hour. After the completion of the reaction, the resultant product is crystallized with ethyl acetate, filtered and dried under reduced pressure, and purified by using normal phase chromatography (250 mg, 2%).

Rf=0.4 (Silica gel, isobutanol/n-propanol/ethyl acetate/water 2:4:1:3 v/v/v/v)

LC/MS, calculated $C_{36}H_{44}N_2Na_2O_{14}S_4$ 902.98, found 901.

Example 9.8

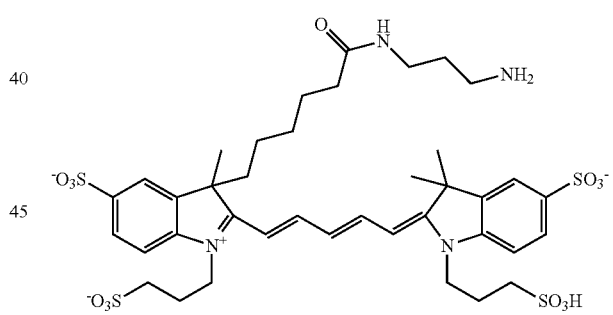

The compound of Example 9.7 (100 mg, 0.1165 mmol, 1 eq), N,N,N',N'-tetramethyl-O—(N-succinimidyl)uronium tetrafluroroborate (TSTU) (77 mL, 0.2563 mmol, 2.2 eq) and triethylamine (125 mg, 0.897 mmol, 7.7 eq) are added to 10 mL of DMF. Next, the mixture is allowed to react at room temperature for 40 minutes. After the reaction, the resultant solid particles are filtered, washed with ethyl acetate three times and dried under reduced pressure. The dried compound and 1,3-diaminopropane (9.72 mg, 0.1165 mmol, 1 eq) are dissolved into 10 mL of DMF and the mixture is allowed to react at room temperature for 30 minutes. After the reaction, the resultant solid particles are filtered, washed with ethyl acetate three times and dried under reduced pressure. Then, purification is carried out by using reverse phase chromatography with 10% acetonitrile to obtain the target compound (91 mg, 86%).

Rf=0.34 (Silica gel, isobutanol/n-propanol/ethyl acetate/water 2:4; 1:3 v/v/v/v)

LC/MS, calculated $C_{39}H_{54}N_4NaO_{13}S_4$ 937.11, found 934.8.

Example 9.9

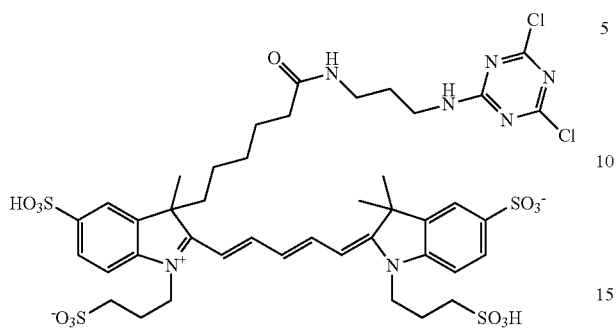

Cyanuric chloride (55 mg, 0.2996 mmol, 3 eq) is introduced into 5 mL of distilled water and 10 g of ice and the mixture is agitated at 0° C. for 0.5 hours. The compound of Example 9.8 (91 mg, 0.0999 mmol, 1 eq) and 5 mg of sodium hydrogen carbonate are added thereto and reaction is carried out at a temperature of 0° C. for 3 hours. After the completion of the reaction, the resultant product is freeze-dried and RP-C18 reverse phase chromatography is carried out by using 20% acetonitrile as an eluent to obtain the target compound (14 mg. 13%).

Rf=0.49 (Silica gel, isobutanol/n-propanol/ethyl acetate/water 2:4; 1;3 v/v/v/v)

LC/MS, calculated $C_{42}H_{52}CO_2N_7O_{13}S_4$ 1062.07, found 1061.4.

Example 9.10

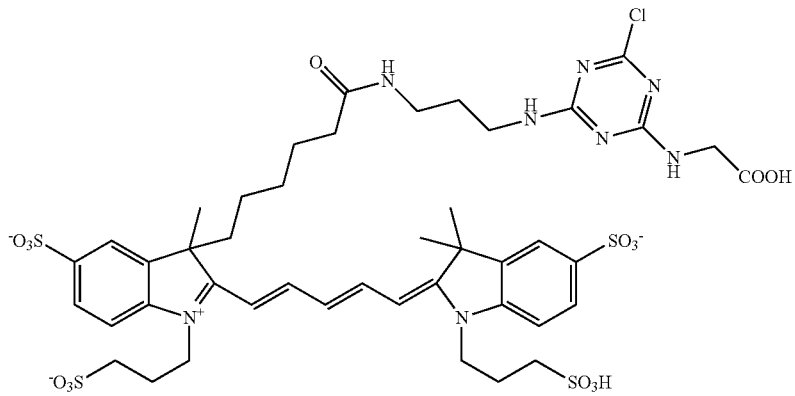

The compound of Example 9.9 (7 mg, 0.0066 mmol, 1 eq), glycine (1.5 mg, 0.0198 mmol, 3 eq) and sodium hydrogen carbonate (1 mg, 0.0132 mmol, 2 eq) are dissolved into 500 μL of distilled water and reaction is carried out at room temperature for 12 hours. After the completion of the reaction, the resultant product is freeze dried and reverse phase chromatography is carried out by using 10% acetonitrile as an eluent to obtain Compound 9 (1 mg, 14%).

Rf=0.31 (Silica gel, isobutanol/n-propanol/ethyl acetate/water 2:4:1:3 v/v/v/v)

LC/MS, calculated $C_{44}H_{54}ClN_8Na_3O_{15}S_4$ 1167.63, found 1167.2.

Example 10

Preparation of Compound 10

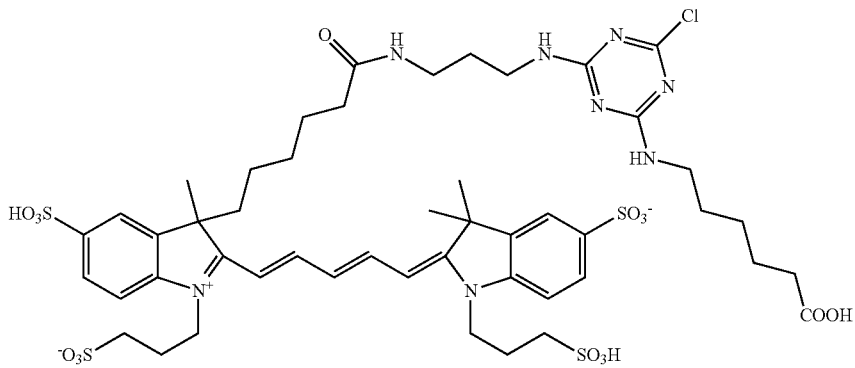

The compound of Example 9.9 (15 mg, 0.014 mmol, 1 eq), 6-aminohexanoic acid (9.27 mg, 0.0707 mmol, 5 eq) and sodium hydrogel carbonate (4.7 mg, 0.056 mmol, 4 eq) are dissolved into 2 mL of distilled water and reaction is carried out at room temperature for 12 hours. After the completion of the reaction, the resultant product is freeze dried and reverse phase chromatography is carried out by using 10% acetonitrile as an eluent to obtain Compound 10 (1.8 mg, 11%).

Rf=0.48 (Silica gel, isobutanol/n-propanol/ethyl acetate/water 2:4:1:3 v/v/v/v)

MALDI-TOF M/S, calculated $C_{48}H_{65}ClN_8O_{15}S_4$ 1157.79, found 1157.4.

Example 11

Preparation of Compound 11

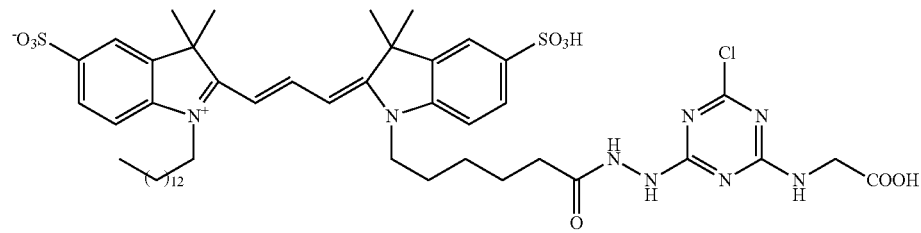

Compound 11 is obtained in a similar manner to the above Examples.

MALDI-TOF M/S, calculated $C_{45}H_{67}ClN_8O_9S_2$ 999.68, found 998.4.

Example 12

Preparation of Compound 12

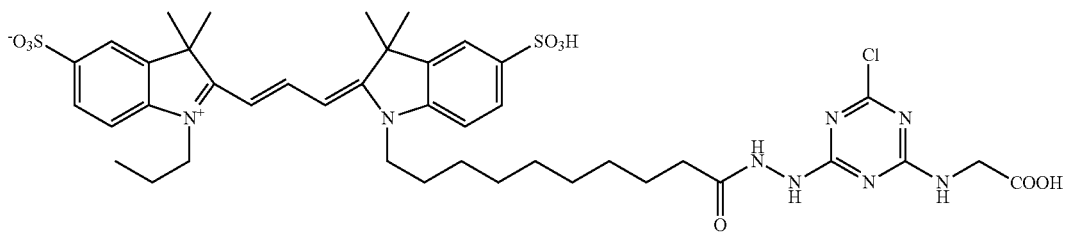

Compound 12 is obtained in a similar manner to the above Examples.
MALDI-TOF M/S, calculated $C_{41}H_{53}ClN_8O_9S_2$ 901.49, found 900.3.

Example 13

Preparation of Compound 13

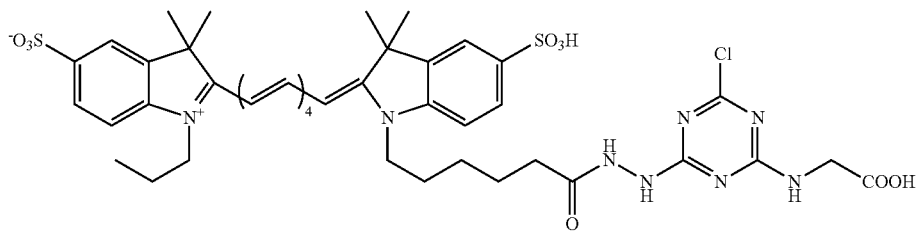

Compound 13 is obtained in a similar manner to the above Examples.
MALDI-TOF M/S, calculated $C_{43}H_{51}ClN_8O_9S_2$ 923.50, found 922.3.

Example 14

Preparation of Compound 14

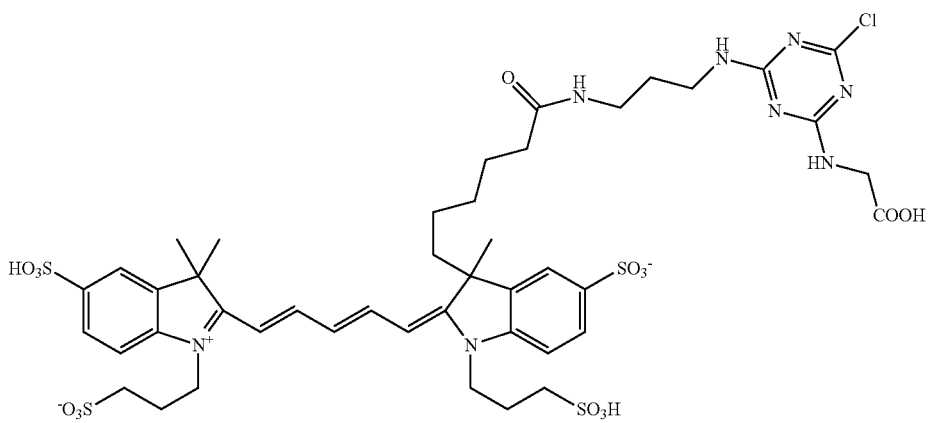

Compound 14 is obtained in a similar manner to the above Examples.
MALDI-TOF M/S, calculated $C_{43}H_{54}ClN_8O_{15}S_4$ 1086.65, found 1085.2.

Example 15

Preparation of Compound 15

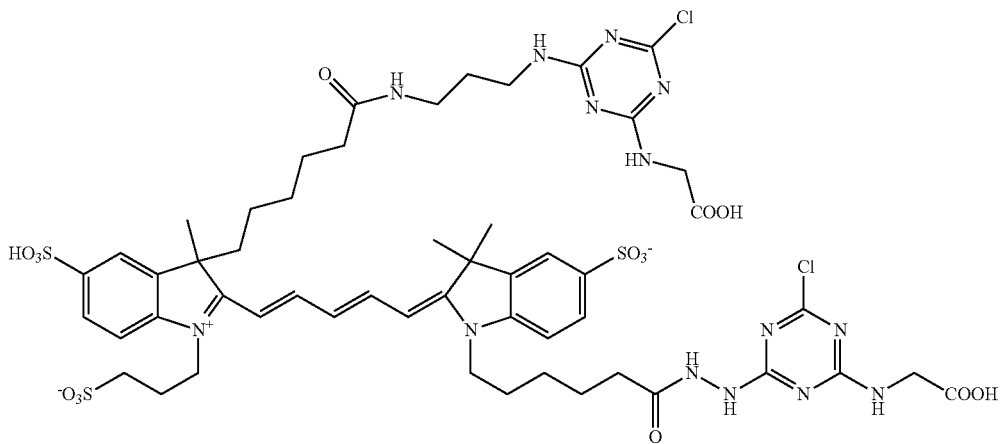

Compound 15 is obtained in a similar manner to the above Examples.

MALDI-TOF M/S, calculated $C_{51}H_{63}ClN_{14}O_{15}S_3$ 1279.23, found 1277.3.

Example 16

Preparation of Compound 16

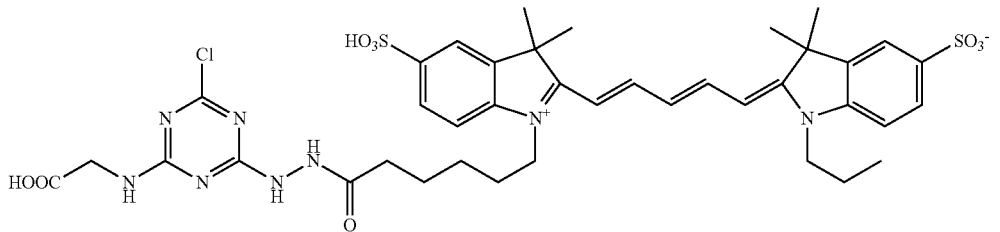

Compound 16 is obtained in a similar manner to the above Examples.

MALDI-TOF M/S, calculated $C_{39}H_{47}ClN_8O_9S_2$ 871.42, found 870.2.

Example 17

Preparation of Compound 17

Example 17.1

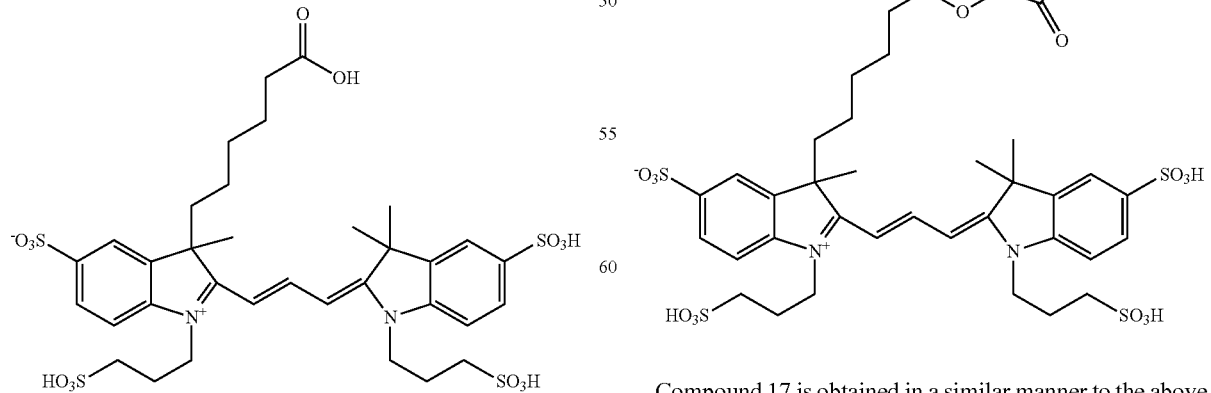

The target compound is obtained in a similar manner to the above Examples.

LC/MS, calculated $C_{34}H_{44}N_2O_{14}S_4$ 832.98, found 831.1.

Example 17.2

Compound 17 is obtained in a similar manner to the above Examples.

LC/MS, calculated $C_{38}H_{47}N_3O_{16}S_4$ 930.05, found 929.8.

Example 18
Preparation of Compound 18
Example 18.1
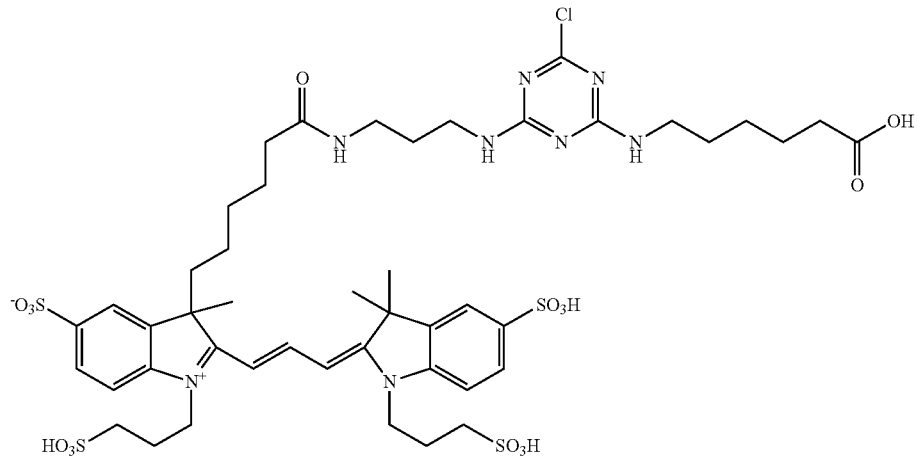
The target compound is obtained in a similar manner to the above Examples.
LC/MS, calculated $C_{46}H_{63}ClN_8O_{15}S_4$ 1130.3, found 1131.5.
Example 18.2
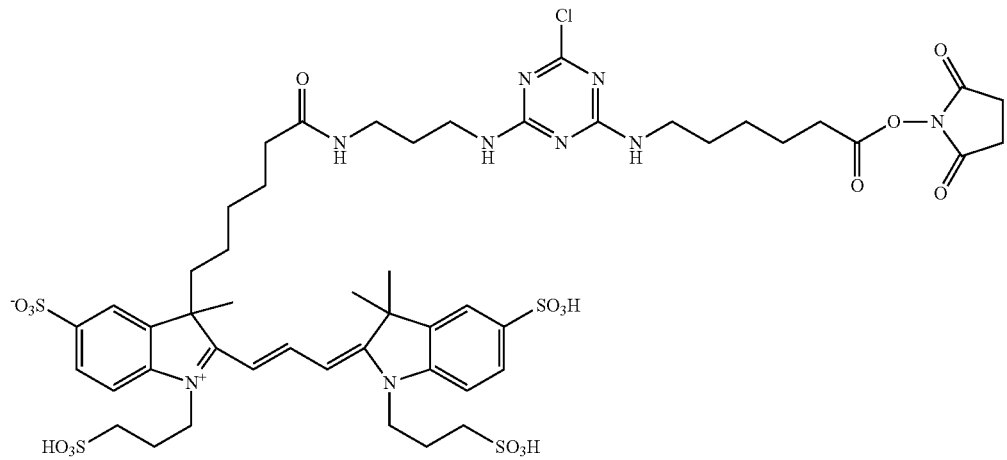
Compound 18 is obtained in a similar manner to the above Examples.
LC/MS, calculated $C_{50}H_{66}ClN_9O_{17}S_4$ 1228.82, found 1226.3.

Example 19

Preparation of Compound 19

Example 19.1

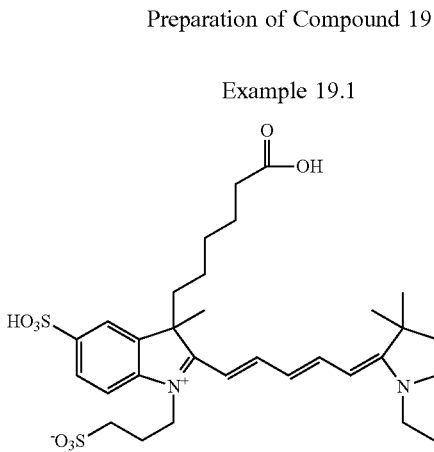

The target compound is obtained in a similar manner to the above Examples.

LC/MS, calculated $C_{36}H_{46}N_2O_{14}S_4$ 859.02, found 858.3.

Example 19.2

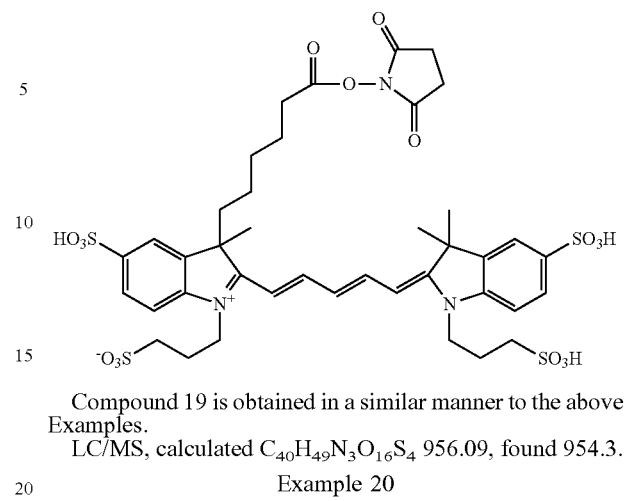

Compound 19 is obtained in a similar manner to the above Examples.

LC/MS, calculated $C_{40}H_{49}N_3O_{16}S_4$ 956.09, found 954.3.

Example 20

Preparation of Compound 20

Example 20.1

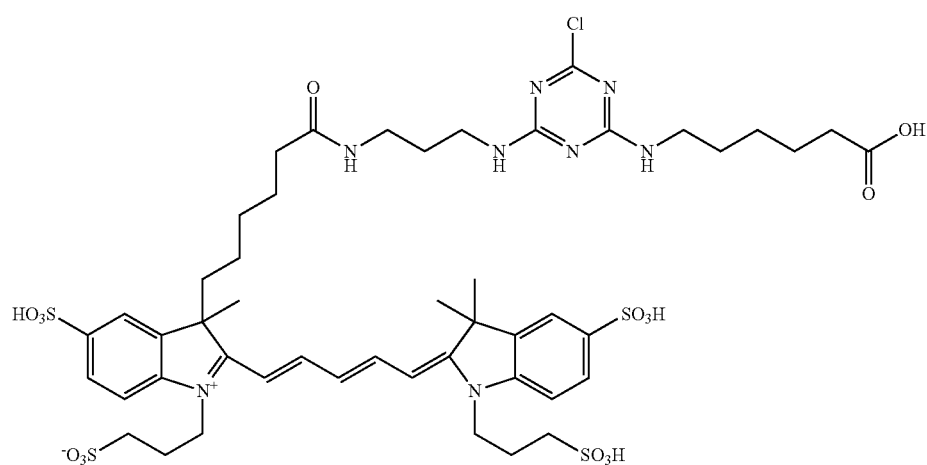

The target compound is obtained in a similar manner to the above Examples.

LC/MS, calculated $C_{48}H_{65}ClN_8O_{15}S_4$ 1157.79, found 1156.0.

Example 20.2

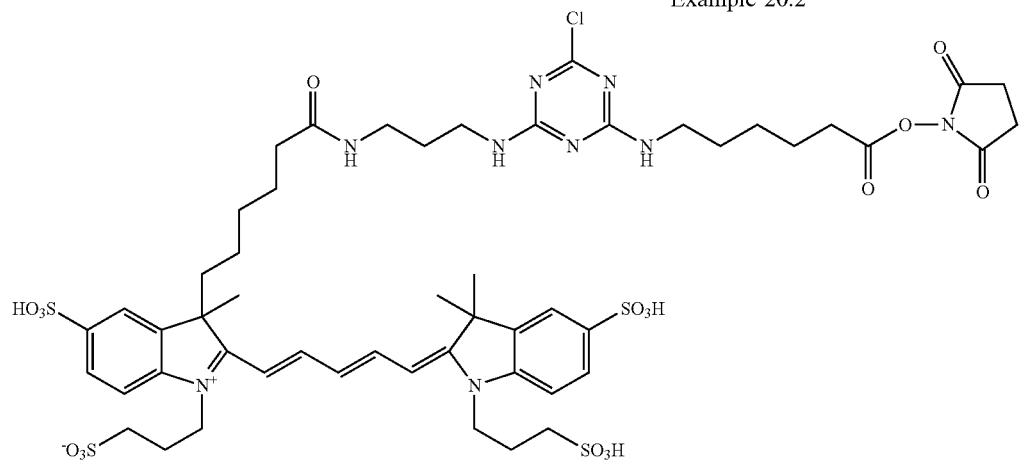

Compound 20 is obtained in a similar manner to the above Examples.

LC/MS, calculated $C_{52}H_{68}ClN_9O_{17}S_4$ 1253.33, found 1253.3.

Comparative Example 1

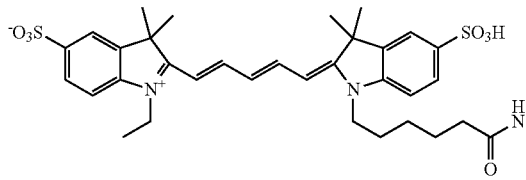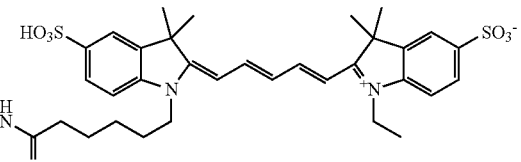

The compound of Example 7.5 (50 mg, 0.061 mmol, 1 eq) is dissolved completely into 3 mL of water and the compound of Example 7.4 (82 mg, 0.122 mmol, 2 eq) is added thereto. Next, the mixture is agitated for 10 minutes and 15 mg of sodium hydrogen carbonate is added thereto, followed by agitation for additional 12 hours. After the completion of the reaction, the resultant product is purified by RP-C18 reverse phase chromatography using 15% aqueous acetonitrile solution as an eluent to obtain the target compound (37 mg, 42%).

Rf=0.6 (Silica gel, acetonitrile/water 9:1 v/v)

Test Example 1

The compound represented by [Chemical Formula 1] disclosed herein includes a cyanine structure having an alkylcarboxyaminocyanuric chloride substituent introduced to the carboxyalkyl residue, and thus shows significantly improved fluorescence intensity as compared to the conventional compound having a cyanine structure.

According to [Chemical Formula 1] disclosed herein, compounds to which a substituent including cyanuric chloride bound with an aminoalkylcarboxylic acid is introduced are prepared and optical properties thereof are compared with each other. Glycine is used as an aminoalkylcarboxylic acid to obtain Compound 1 (Example 1.7) disclosed herein, and the optical properties thereof are compared with those of the compound (Example 1.3) including no alkylcarboxyamino cyanuric chloride substituent introduced thereto.

At the same concentration, the compounds of Example 1.7 and Example 1.3 are determined for absorption wavelength and intensity and the results are shown in FIG. 1A. The compound of Example 1.3 shows slightly higher absorption wavelength intensity. To perform accurate comparison of fluorescence wavelength intensity, the concentration of each of the compounds of Example 1.7 and Example 1.3 is corrected so that they may have the same absorption intensity, and then the fluorescence wavelength and intensity of each compound are determined. The results are shown in FIG. 1B.

As shown in FIG. 1B, it can be seen that the cyanine-based compound (Example 1.7) including an alkylcarboxyaminocyanuric chloride substituent according to an embodiment shows intensity of fluorescence wavelength approximately two times higher than that of the cyanine-based compound (Example 1.3) including no alkylcarboxyaminocyanuric chloride substituent.

Test Example 2

To determine a change in optical properties when the compound of [Chemical Formula 1] disclosed herein is modified to allow labeling of a biomolecule, an N-succinimidyl group is introduced to each of Compound 9.7 and Compound 10 to obtain Compound 19 and Compound 20, respectively, in the same manner as described hereinabove. Then, fluorescence characteristics are compared at the same absorption wavelength intensity.

Comparison of Fluorescence Characteristics at the Same Absorption Wavelength and Intensity Each of Compound 19 and Compound 20 is added to 5 mL of PBS at a concentration of 10 mg/mL at room temperature to provide samples. Next, 1 mL of PBS is added to 2 mL of each sample and the intensity is measured as a function of absorption wavelength. After adjusting the concentration of a sample so that the absorption intensity (Abs at 650 nm) of Compound 19 may be the same as that of Compound 20 from the resultant data, the sample is diluted many times and the fluorescence thereof is determined by using a plate reader (Perkin Elmer). Three measurements of fluorescence are averaged and the results are shown in the following Table 1 and Table 2. Table 1 shows the results of fluorescence intensity of Compound 19 as a function of concentration and Table 2 shows those of Compound 20 as a function of concentration.

Figure 2:
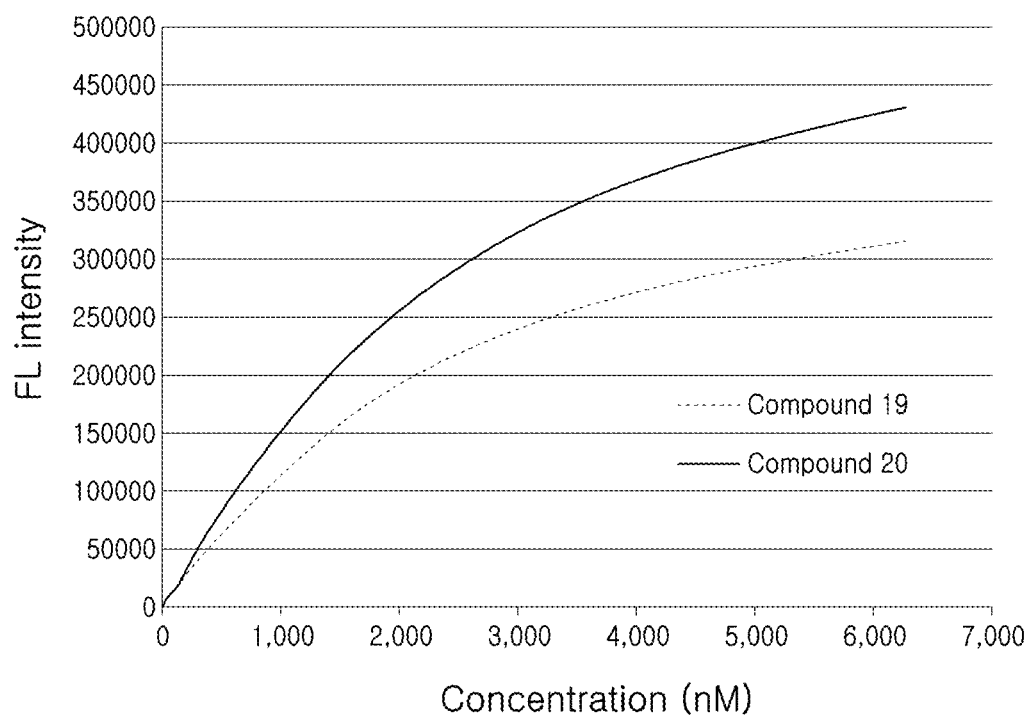
FIG. 2 shows the results of evaluation of optical properties depending on the introduction of an alkylcarboxyaminocyanuric chloride substituent according to another embodiment.

It can be seen that Compound 20, a compound of [Chemical Formula 1] disclosed herein, shows significantly improved fluorescence intensity as compared to Compound 19. As shown in FIG. 2, a difference in fluorescence intensity becomes larger as the concentration increases, and an increment of about 40% is shown at a concentration of 7M. It can be seen from the above results that the compound of [Chemical Formula 1] disclosed herein retains significantly improved fluorescence characteristics even after being modified for the purpose of labeling of a biomolecule.

TABLE 1

| Concentration (nM) | Average fluorescence intensity (at 665 nm) | Standard |
|---|---|---|
| 6280 | 308345.7 | 6239.5 |
| 3140 | 240494.7 | 5760.9 |
| 1570 | 160778.3 | 2481.3 |
| 785 | 91308.7 | 1273.9 |
| 393 | 48611.7 | 1555.6 |
| 196 | 24679.7 | 11.5 |
| 98 | 12523.0 | 205.9 |
| 49 | 6483.7 | 129.6 |
| 25 | 3336.7 | 49.6 |
| 12 | 1673.0 | 34.8 |
| 6 | 810.7 | 48.2 |
| 3 | 412.0 | 11.2 |

TABLE 2

| Concentration (nM) | Average fluorescence intensity (at 665 nm) | Standard |
| --- | --- | --- |
| 6280 | 418428.3 | 10381.1 |
| 3140 | 321865.0 | 7104.5 |
| 1570 | 209850.3 | 6726.9 |
| 785 | 118049.0 | 4875.9 |
| 393 | 59756.7 | 2979.6 |
| 196 | 29396.3 | 1713.1 |
| 98 | 13859.7 | 1097.1 |
| 49 | 6693.3 | 443.8 |
| 25 | 2994.3 | 278.8 |
| 12 | 1454.7 | 137.8 |
| 6 | 721.3 | 78.8 |
| 3 | 313.3 | 64.1 |

Test Example 3

The compound of [Chemical Formula 1] disclosed herein is used for labeling a biomolecule in vitro and the fluorescence characteristics are evaluated.

To 0.1 M phosphate-carbonate buffer at pH 9.0, monoclonal antibody immunoglobulin G extracted from the immune cells of a mouse is dissolved to a concentration of 2 mg/mL and the solution is pipetted in a tube in an amount of 100 μL to provide six samples. Each of Compound 19 and Compound 20 is dissolved into dimethyl formamide at a concentration of 10 mg/mL. Then, each of Compound 19 and Compound 20 is added to the six sample tubes in an amount of 2.0, 2.5 and 3.0 L, followed by agitation at room temperature for 60 minutes, to carry out labeling.

Each antibody solution after the completion of the labeling is purified with a dextran column and adjusted to the same antibody concentration. Then, the fluorescence spectrum of each labeled antibody solution is determined and used for comparison of a change in fluorescence intensity depending on added amount of a fluorescent dye. The results are shown in FIG. 3.

Figure 3:
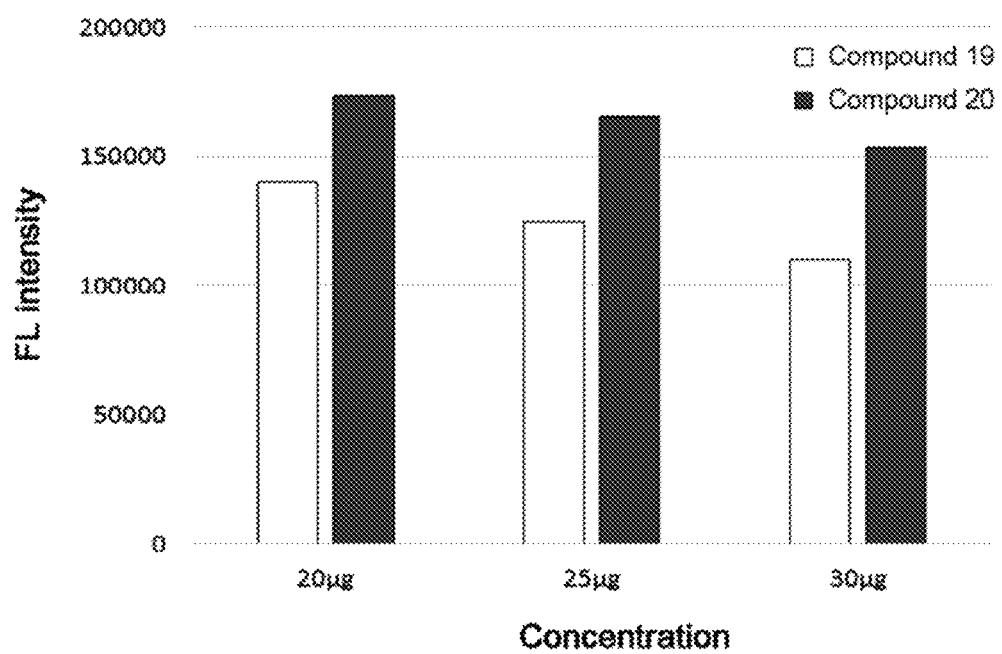
FIG. 3 shows the results of determination of improved optical properties after a biosubstance is labeled with a compound according to an embodiment.

Referring to FIG. 3, when immunoglobulin G is labeled with Compound 20, fluorescence intensity is increased by approximately 30% on average as compared to Compound 19.

In other words, the compound of [Chemical Formula 1] disclosed herein shows significantly improved fluorescence intensity as compared to the conventional structure, even after being used for labeling a biomolecule.

Test Example 4

Figure 4:
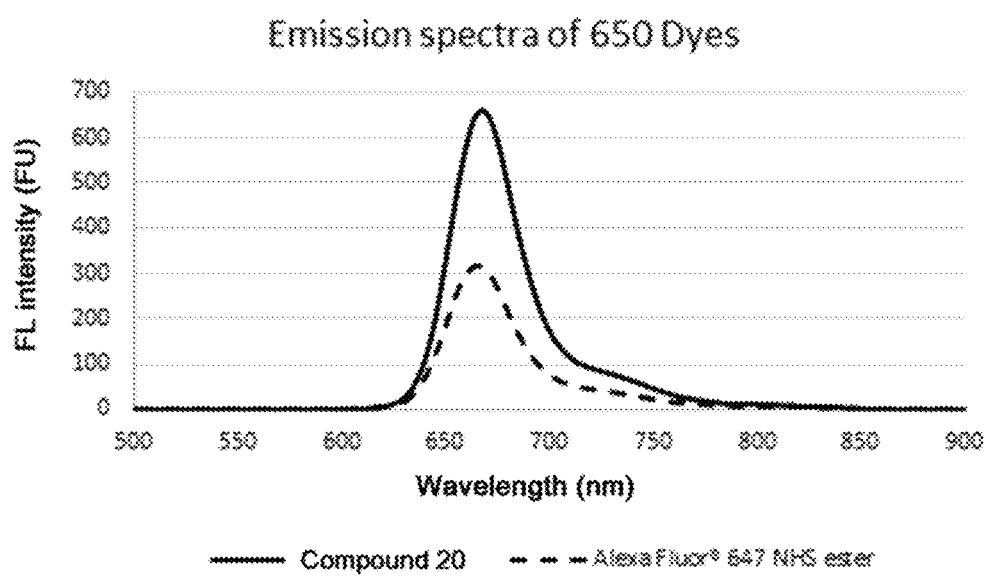
FIG. 4 shows the fluorescence spectrum of Compound 20 and that of a reference fluorescent dye.

Evaluation of Optical Properties of Compounds (1) Comparison of Fluorescence Intensity—650 Wavelength Dyes Compound 20 and a reference fluorescent dye (Alexa Fluor 647 NHS ester) are compared with each other in terms of fluorescence intensity. DMF is added to the two types of fluorescent dyes to provide stock solutions and each solution is adjusted to the same concentration of 10 mg/mL. Next, pH 7.4 10 mM phosphate buffered saline (hereinafter, 1×PBS) is used to dilute the solution to a concentration of 19.5 nM and fluorescence is determined under the setting of Excitation 560 nm. The fluorescence determination is carried out by using LS 55 Fluorescence spectrometer (Perkin Elmer). FIG. 4 shows the fluorescence spectrum of Compound 20 and that of the reference fluorescent dye. It can be seen from this analysis that Compound 20 has relatively higher fluorescence intensity.

(2) Comparison of Fluorescence Intensity—552 Wavelength Dyes

Figure 5:
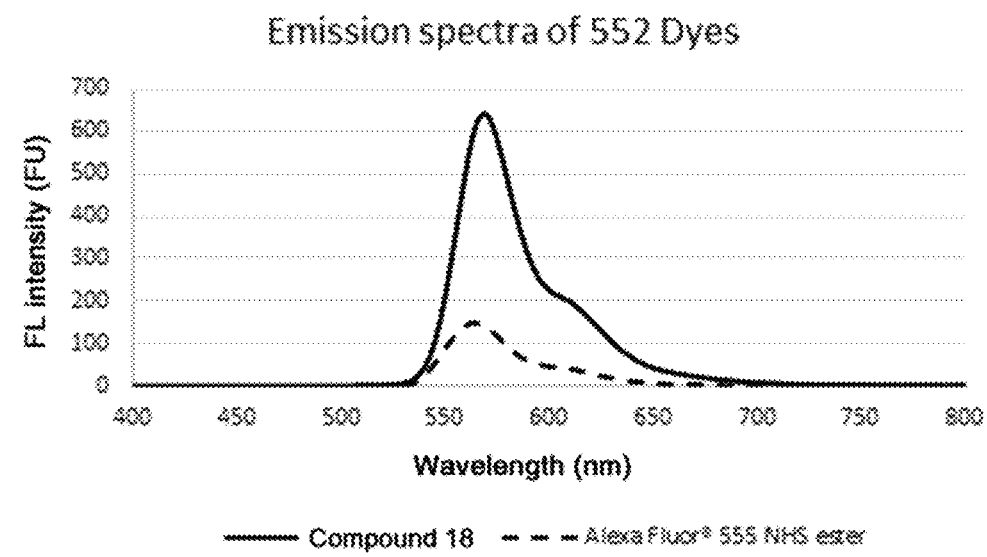
FIG. 5 shows the fluorescence spectrum of Compound 18 and that of a reference fluorescent dye.

Compound 18 and a reference fluorescent dye (Alexa Fluor 555 NHS ester) are compared with each other in terms of fluorescence intensity. DMF is added to the two types of fluorescent dyes to provide stock solutions and each solution is adjusted to the same concentration of 10 mg/mL. Next, pH 7.4 10 mM phosphate buffered saline (hereinafter, 1×PBS) is used to dilute the solution to a concentration of 19.5 nM and fluorescence is determined under the setting of Excitation 552 nm. The fluorescence determination is carried out by using LS 55 Fluorescence spectrometer (Perkin Elmer). FIG. 5 shows the fluorescence spectrum of Compound 18 and that of the reference fluorescent dye. It can be seen from this analysis that Compound 18 has relatively higher fluorescence intensity.

(3) Determination of Relative Quantum Yield of 650 Compound

Figure 6:
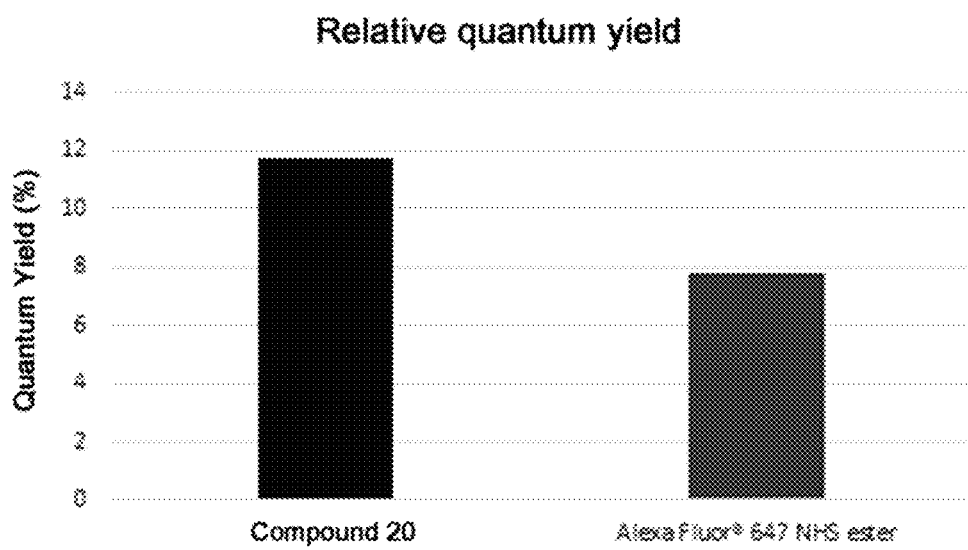
FIG. 6 shows the results of determination of relative quantum yield of Compound 20 and that of a reference fluorescent dye.

Based on Rhodamine 6G (TCI), relative quantum yield of Compound 20 and that of the reference fluorescent dye (Alexa Fluor 647 NHS ester) are determined. DMF is added to the two types of fluorescent dyes and Rhodamine 6G to 10 mg/mL to provide stock solutions. Next, pH 7.4 1×PBS is used to dilute the solutions to a concentration of 10 μM and absorption and fluorescence are determined. Herein, 1/2 dilution is carried out from a concentration of 10 μM and then absorption and fluorescence are determined 10 times totally up to the sample of 1/512× concentration. The determined values are introduced to the following Mathematical Formula 1 to analyze the relative quantum yield and the results are shown in the following Table 3 and FIG. 6. It can be seen that Compound 20 shows a higher relative quantum yield as compared to the reference fluorescent dye.

[Mathematical Formula 1]

$$Q = Q_R \frac{I}{I_R} \frac{OD_R}{OD} \quad (1)$$

Q=Quantum Yield
I=Fluorophore
OD=Absorbance
Subscript$_R$=Rodamine 6G

TABLE 3

| | Compound 20 | Alexa 647 NHS ester |
| --- | --- | --- |
| Relative quantum yield (%) | 11.70 | 7.79 |

(4) Determination of Relative Quantum Yield of 552 Compound

Figure 7:
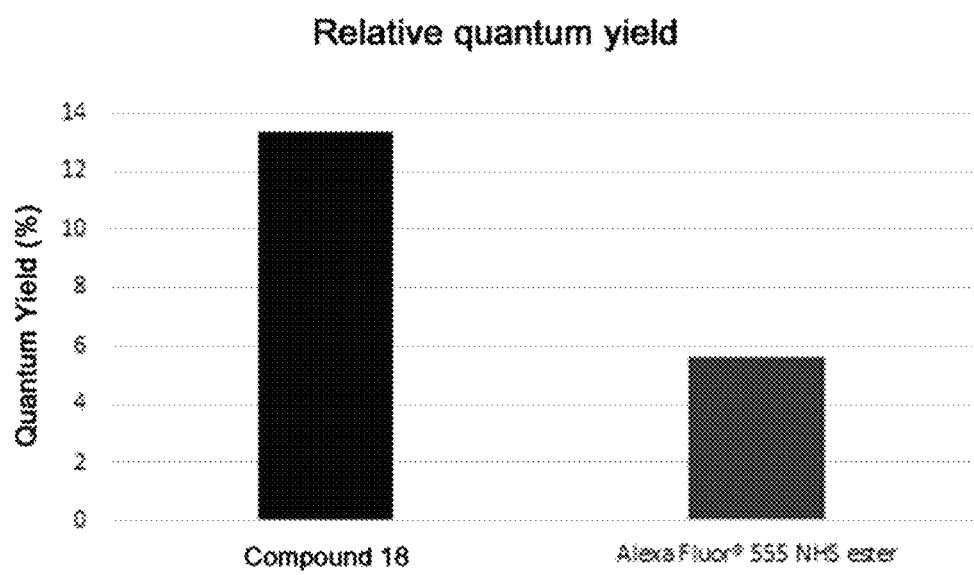
FIG. 7 shows the results of determination of relative quantum yield of Compound 18 and that of a reference fluorescent dye.

Based on Rhodamine 6G (TCI), relative quantum yield of Compound 18 and that of the reference fluorescent dye (Alexa Fluor 555 NHS ester) are determined. DMF is added to the two types of fluorescent dyes and Rhodamine 6G to 10 mg/mL to provide stock solutions. Next, pH 7.4 1×PBS is used to dilute the solutions to a concentration of 10 μM and absorption and fluorescence are determined. Herein, 1/2 dilution is carried out from a concentration of 10 μM and then absorption and fluorescence are determined 10 times totally up to the sample of 1/512× concentration. The determined values are introduced to Mathematical Formula 1 to analyze the relative quantum yield. The following Table 4 and FIG. 7 show the relative quantum yield of each dye. It can be seen that Compound 18 shows a higher relative quantum yield based on Rhodamine 6G.

TABLE 4

| | Compound 18 | Alexa 555 NHS ester |
|---|---|---|
| Relative quantum yield (%) | 13.34 | 5.64 |

Test Example 5

Figure 8:
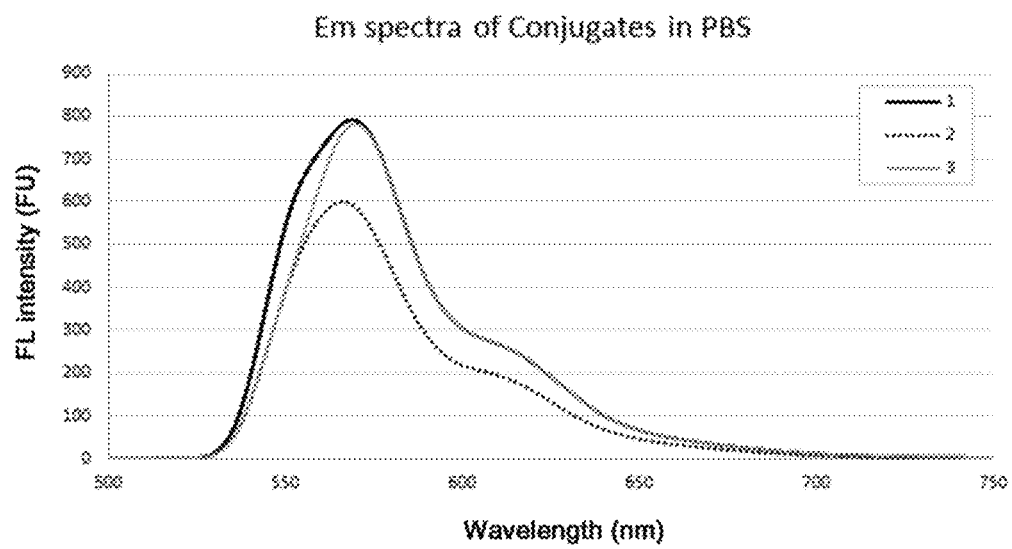
FIG. 8 shows the results of comparison of fluorescence intensity of protein conjugates between Compound 18 and a reference fluorescent dye.

Comparison of Properties after Labeling of Protein (1) Comparison of Fluorescence Intensity Between Protein Conjugates of 552 Wavelength Dyes Compound 18 and the reference fluorescent dye (Alexa Fluor 555 NHS ester) are used to label an antibody (Pierce™ Gt anti-Ms IgG H+L Secondary Ab, 10 mg/mL, Thermo) and the resultant conjugates are compared with each other in terms of fluorescence intensity. Each of Compound 18 and the reference fluorescent dye is dissolved into DMF to provide a stock solution at 10 mg/mL. Samples 1 and 2 are obtained from 0.5 mg of the antibody through the reaction ratio with a dye of 25 mol and Sample 3 is prepared through the reaction with 0.083 mg of Compound 18 in order to further determine the result obtained under the same weight ratio based on the reference fluorescent dye. The test conditions are shown in the following Table 5 and the results are shown in FIG. 8.

TABLE 5

| Sample No. | Compound | Molecular weight (g/mol) | Reacted amount of dye (uL) | D/P ratio |
|---|---|---|---|---|
| 1 | Compound 18 | 1227.30 | 10.96 | 8.42 |
| 2 | Alexa 555 NHS ester | 929.18 | 8.30 | 8.71 |
| 3 | Compound 18 | 1227.30 | 8.30 | 7.12 |

The final reaction concentration of the antibody is set to 2 mg/mL and a reaction buffer is prepared by mixing 10 mM phosphate buffered saline (hereinafter, 1×PBS) with pH 9.4 1M sodium-carbonate-bicarbonate buffer (hereinafter, 1M CBC) so that the final pH may be about 8.3-8.5. Samples 1-3 are allowed to react under room temperature/dark chamber/agitation conditions for 1 hour, and purified through a column filled with Sephadex G-25 resin (GE Healthcare) to isolate the conjugates. The resin is subjected to buffer equilibrium (buffer change) with 1×PBS before its use. At a wavelength of 280/552 nm, each conjugate is subjected to absorption spectrometry (Cary 8454 UV-Vis spectrophotometer, Agilent) to determine the Dye/Protein ratio (D/P ratio) first. Next, the conjugates are determined for fluorescence (LS 55 Fluorescence spectrometer, Perkin Elmer) to carry out comparison of fluorescence intensity. Fluorescence determination is carried out by mixing each conjugate with 3 mL of 1×PBS to perform dilution and then under the setting of Excitation 552 nm. As shown in FIG. 8, The Ab conjugates of Compound 18 shows higher fluorescence intensity regardless of the amount of dye.

Figure 9:
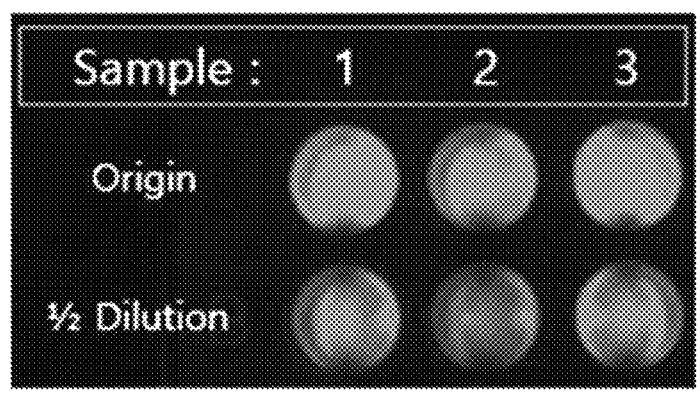
FIG. 9 shows the results of fluorescence intensity analysis using fluorescence in vivo imaging (FOBI).

FIG. 9 shows the fluorescence intensity analysis results using fluorescence in vivo imaging system (FOBI, neoscience). The same results can be seen herein. The first line shows the analysis results of the non-diluted original conjugate sample and the second line shows those of the sample subjected to 1/2 dilution with 1×PBS under the application of light source green channels, after each sample is introduced in an amount of 100 μL per well.

(2) Labeling Ratio of 650 Wavelength Dye Depending on Reacted Amount of Dye

Figure 10:
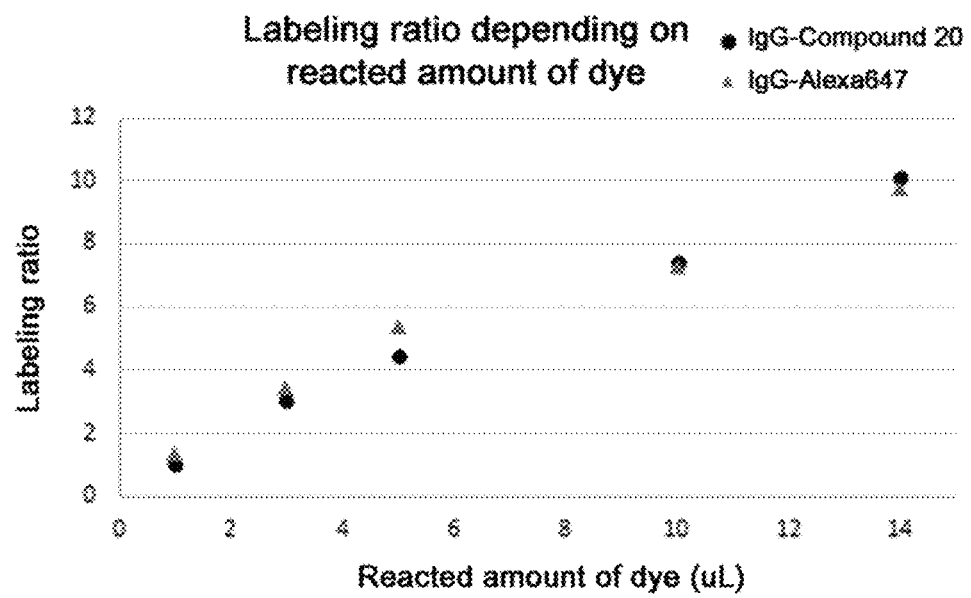
FIG. 10 shows the results of comparison of labeling ratio (D/P ratio) as a function of reacted amount of dye between Compound 20 and a reference fluorescent dye.

Each of Compound 20 and the reference fluorescent dye (Alexa Fluor 647 NHS ester) is used for labeling 0.5 mg of an antibody (Pierce™ Gt anti-Rb IgG H+L Secondary Ab, 10 mg/mL, Thermo) at a different weight ratio. The results of comparison of labeling ratio (D/P ratio) depending on the amount of a dye are shown in FIG. 10. For reference, Compound 20 has a molecular weight of 1254.7 g/mole and the reference fluorescent dye has a molecular weight of 956.1 g/mole. The same labeling method as Test Example 5-(1) is repeated, except that the amount of a dye is set to 0.01, 0.03, 0.05, 0.10 or 0.14 mg. Each conjugate isolated after the labeling and purification is analyzed for absorbance at a wavelength of 280/650 nm, and the generally known mathematical formula is used to calculate labeling ratios. For Compound 20 and the reference fluorescent dye, a molar absorption coefficient of 239,000/cmM (in PBS), a protein molar absorption coefficient of 203,000/cmM and a correction factor ($CF_{280}$) of 0.03 are used. The results are shown in Table 6. It can be seen that both of Compound 20 and the reference fluorescent dye provide a gradually increased labeling ratio as the amount is increased. When at least 0.10 mg (about 25 moles after molar conversion) of a dye is reacted without application of molar ratio, the labeling ratio of Compound 20 starts to be higher than that of the reference fluorescent dye. In addition, as mentioned above, Compound 20 has a molecular weight of 1254.7 g/mole which is larger than the molecular weight (956.1 g/mole) of the reference fluorescent dye (by about 30% or more). Thus, even though Compound 20 and the reference fluorescent dye are used at the same weight, Compound 20 is introduced in a relatively smaller molar number as compared to the reference fluorescent dye. Therefore, Compound introduced at a smaller molar number shows an equivalent or higher effect as compared to the reference fluorescent dye, and thus is at least equivalent to the reference fluorescent dye in terms of a labeling effect.

TABLE 6

| Product | Protein (Final conc. 2 mg/mL) | Dye (10 mg/mL) | D/P ratio |
|---|---|---|---|
| Compound 20 | Ab 0.5 mg | 0.14 mg (14 uL) | 10.13 |
| | | 0.10 mg (10 uL) | 7.40 |
| | | 0.05 mg (5 uL) | 4.45 |
| | | 0.03 mg (3 uL) | 3.01 |
| | | 0.01 mg (1 uL) | 1.04 |
| Alexa Fluor 647 NHS ester | Ab 0.5 mg | 0.14 mg (14 uL) | 9.76 |
| | | 0.10 mg (10 uL) | 7.27 |
| | | 0.05 mg (5 uL) | 5.37 |
| | | 0.03 mg (3 uL) | 3.42 |
| | | 0.01 mg (1 uL) | 1.35 |

(3) Fluorescence Intensity of 650 Wavelength Dye Depending on Reacted Amount

Figure 11:
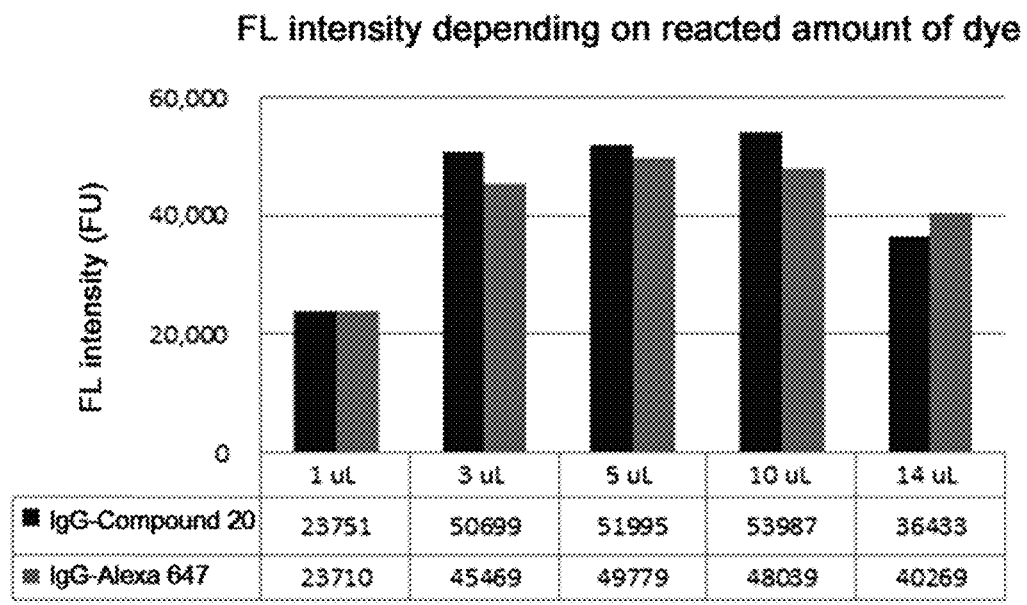
FIG. 11 shows the results of comparison of fluorescence intensity as a function of reacted amount of dye between Compound 20 and a reference fluorescent dye upon the labeling of a protein.
Figure 12:
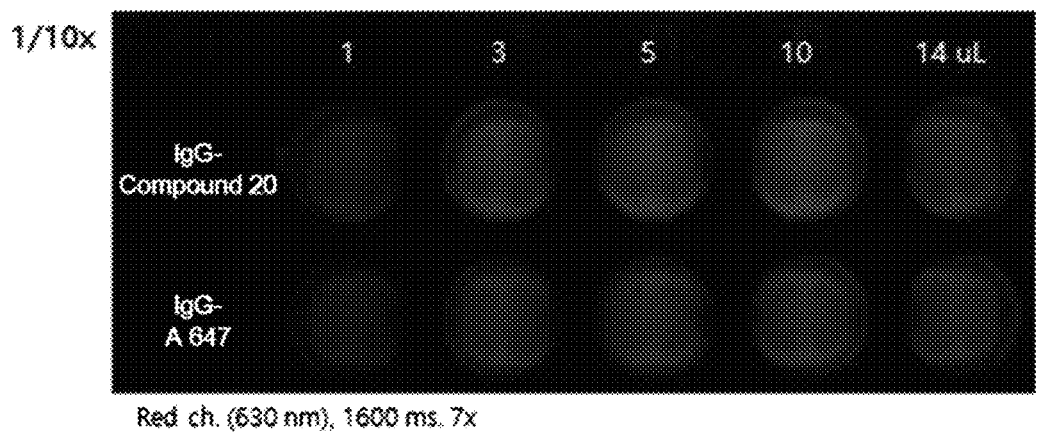
FIG. 12 shows the results of imaging in the FOBI red channel.

The conjugates extracted from Test Example 5-(2) are used to compare the fluorescence intensity of Compound 20 with that of the reference fluorescent dye upon the labeling of a protein as a function of reacted amount. The results are shown in FIG. 11 and the imaging results thereof are shown in FIG. 12. To the first line and the second line of a 96-well black plate, [IgG-Compound 20] conjugate and [IgG-reference fluorescent dye] conjugate is injected after diluting each conjugate at a ratio of 1/10 in the order of dye amount. To the fourth line, 1×PBS is introduced as a blank. All analytical samples are introduced in an amount of 100 μL and the protein concentration is the same with a neglectable error. Then, imaging is carried out in an FOBR Red channel and analysis based on a multilabel plate reader (Enspire 2300, Perkin Elmer) is performed in order to accomplish more accurate numerical comparison. Determination is carried out under adequate setting conditions including Ex. 650 nm/Em. 655 nm, a number of flashes of 200, or the like. In a region of reacted amount of dye of 0.03, 0.05 and 0.10 mg, relatively strong fluorescence is observed and Compound 20 conjugates show higher fluorescence intensity up to a reacted amount of dye of 0.10 mg (10 mg/mL). The maximum fluorescence intensity is determined when 0.5 mg of the antibody reacts with 0.1 mg of Compound 20. When the reaction amount of Compound 20 is merely 0.03 mg, the fluorescence intensity is similar to the maximum value. Thus, it is expected that, Compound 20 is excellent as compared to the reference fluorescent dye and may show higher fluorescence even when used in a smaller amount for labeling a biomolecule. In addition, with reference to the tendency of maintenance in fluorescence intensity depending on the reacted amount of dye, the reference fluorescent dye shows a decrease in intensity after 0.05 mg. However, Compound 20 shows a continuous increase in intensity even up to 0.10 mg. Thus, it is demonstrated that Compound 20 provides an excellent effect.

(4) Fluorescence Intensity Depending on Labeling Ratio of 650 Wavelength Dye

Figure 13:
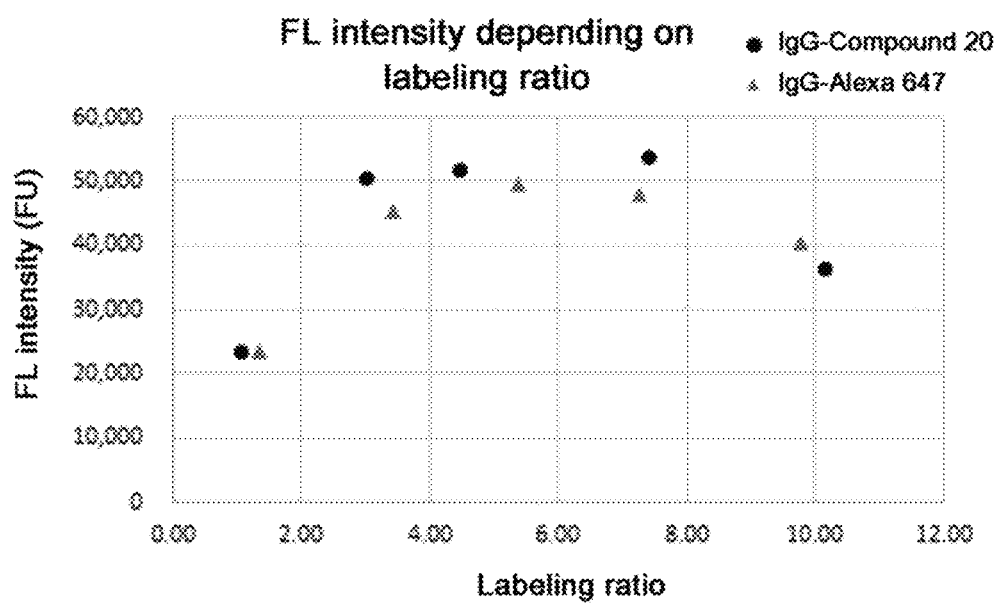
FIG. 13 shows the results of fluorescence intensity as a function of labeling ratio between Compound 20 and a reference fluorescent dye.

Based on the results of Test Examples 5-(2) and 5-(3), the fluorescence intensity of each of Compound 20 and the reference fluorescent dye depending on labeling ratio is shown in FIG. 13. It can be seen from the above results that Compound 20 having a larger molecular weight shows a similar level of labeling ratio to the reference fluorescent dye, when carrying out reaction with a protein at the same weight ratio. It can be also seen that even when the reacted amount of dye is smaller, i.e., when the labeling ratio is lower, Compound 20 accomplishes higher fluorescence intensity as compared to the reference fluorescent dye. It can be seen from FIG. 13 that Compound 20 disclosed herein shows slower auto-quenching through the comparison between the protein labeled with Compound 20 and the protein labeled with the reference fluorescent dye. In the case of the reference fluorescent dye, auto-quenching proceeds form a relatively low labeling ratio of about 6.

What is claimed is:

1. A fluorescent compound represented by the following [Chemical Formula 1]:

[Chemical Formula 1]

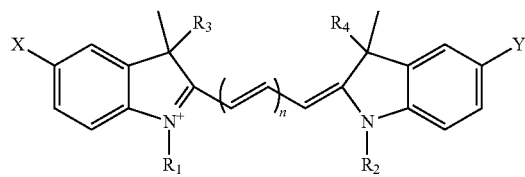

wherein X and Y are the same or different, and each is independently selected from H, —$SO_3$— and —$SO_3H$;

$R_1$ and $R_2$ are the same or different, and each is selected from $C_{1-7}$ alkyl, $C_{8-18}$ alkyl, —$(CH_2)_mSO_3^-$, —$(CH_2)_mSO_3H$, and

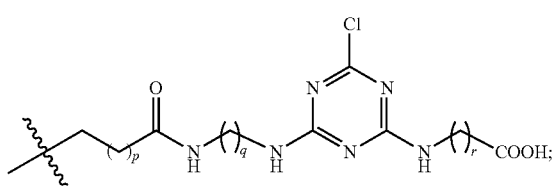

$R_3$ and $R_4$ are the same or different, and each is selected from $C_{1-7}$ alkyl, —$(CH_2)_mCOOZ_1$ and

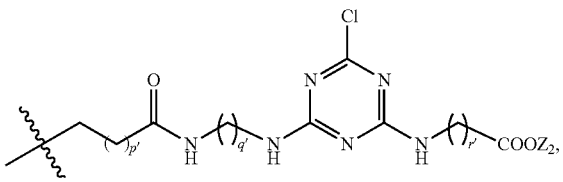

with the proviso that both of $R_3$ and $R_4$ cannot represent any one selected from —$(CH_2)_mCOOZ_1$ and

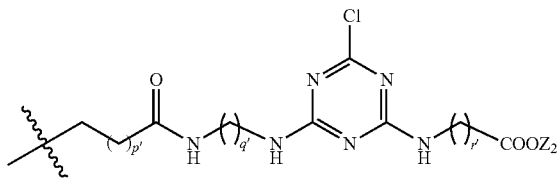

at the same time;

$Z_1$ and $Z_2$ are the same or different, and each is independently substituted with a substituent selected from H, N-succinimidyl, hydrazinyl, N-hydroxysuccinimidyl, N-hydrosuccinimidyloxy, sulfosuccinimidyloxy, 4-sulfo-2,3,4,5-tetrafluorophenyl, maleinimide $C_{0-10}$alkylaminyl, vinylsulfonyl, vinylsulfonyl $C_{0-6}$alkylaminyl and amino$C_{0-6}$alkyl;

n is an integer of 1-6;
m is an integer of 1-7;
p is an integer of 1-10;
q is an integer of 0-6;
r is an integer of 1-10;
m' is an integer of 1-7;
p' is an integer of 1-10;
q' is an integer of 1-10; and
r' is an integer of 1-10;

wherein at least one of $R_1$ and $R_2$ is

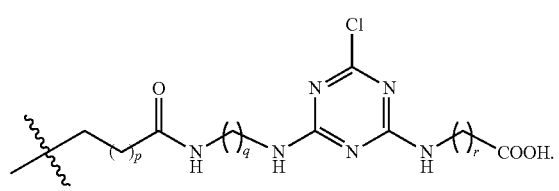

or each of $R_3$ and $R_4$ is

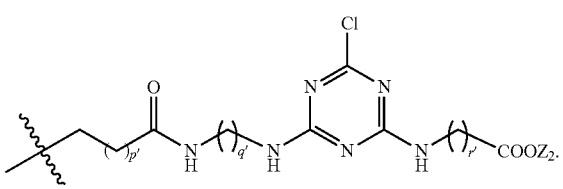

2. The fluorescent compound according to claim 1, wherein $R_1$ and $R_2$ are the same or different, and each is selected from $C_{1-7}$ alkyl, $C_{8-18}$ alkyl, —$(CH_2)_mSO_3^-$, —$(CH_2)_mSO_3H$, and

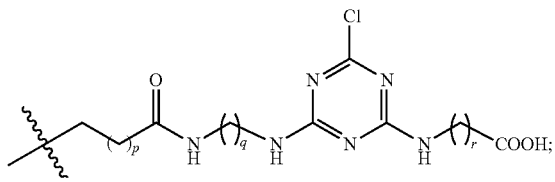

$R_3$ and $R_4$ are the same or different, and each is selected from $C_{1-7}$ alkyl, $-(CH_2)_m COOZ_1$ and

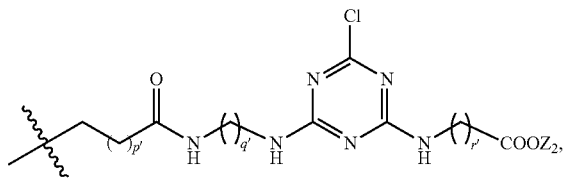

with the proviso that both of $R_3$ and $R_4$ cannot represent any one selected from $-(CH_2)_m COOZ_1$ and

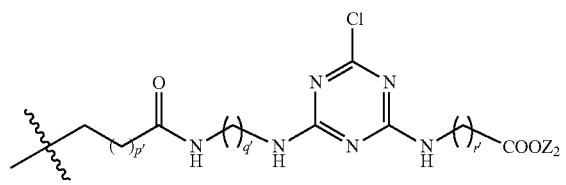

at the same time;

$Z_1$ and $Z_2$ are the same or different, and each independently represents H or N-succinimidyl;

n is an integer of 1-6;
m is an integer of 1-6;
p is an integer of 3-7;
q is an integer of 0-4;
r is an integer of 1-6;
m' is an integer of 1-7;
p' is an integer of 3-7;
q' is an integer of 1-6; and
r' is an integer of 1-7.

3. The fluorescent compound according to claim 1, wherein at least one of $R_1$ and $R_2$ represents

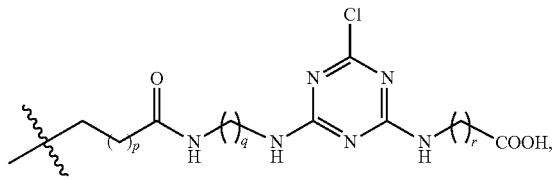

and at least one of $R_3$ and $R_4$ represents $-(CH_2)_m COOZ_1$ or

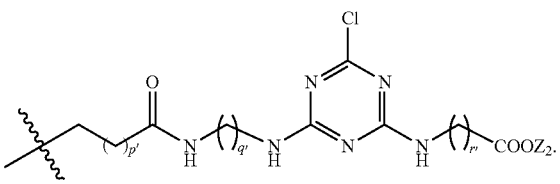

4. The fluorescent compound according to claim 1, wherein the compound represented by [Chemical Formula 1] is selected from:

Compound 1

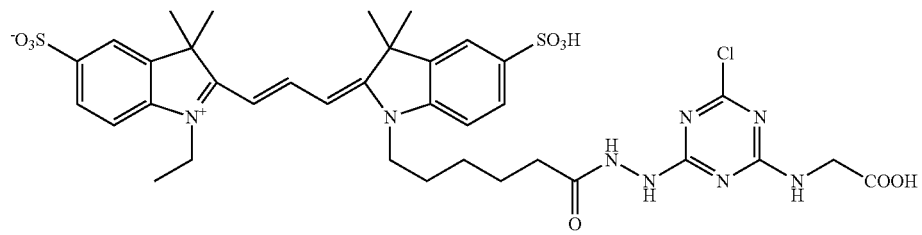

Compound 2

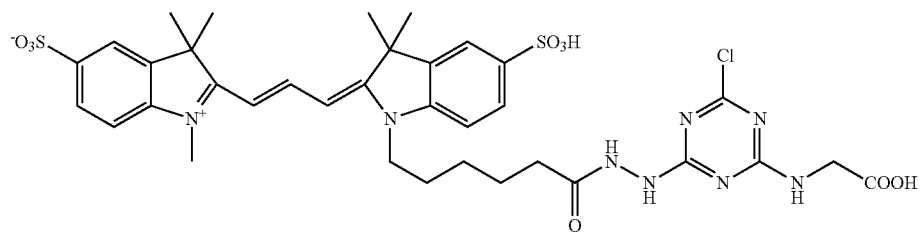

Compound 3

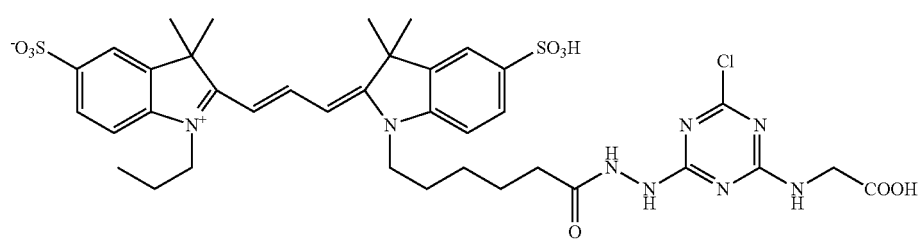

Compound 4
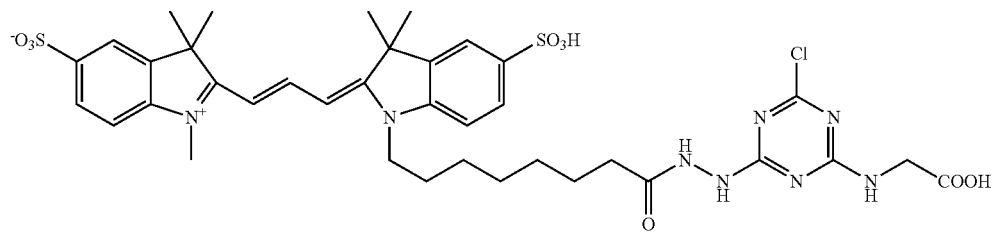
Compound 5
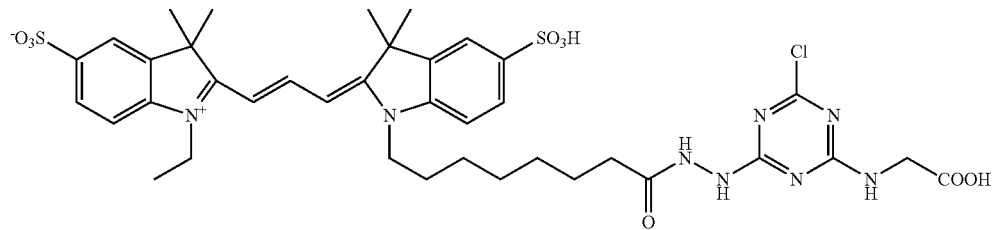
Compound 6
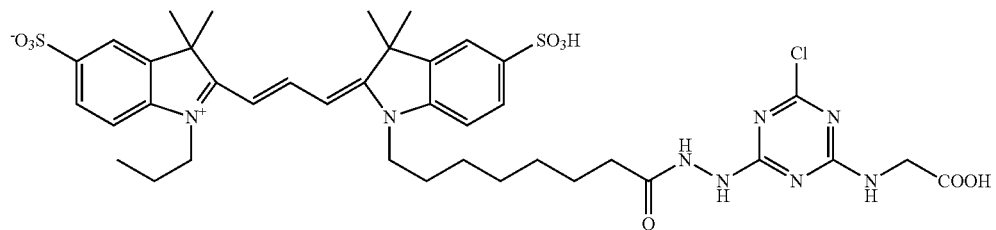
Compound 7
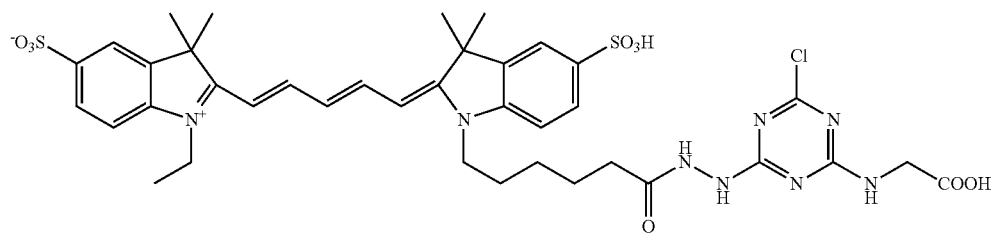
Compound 8
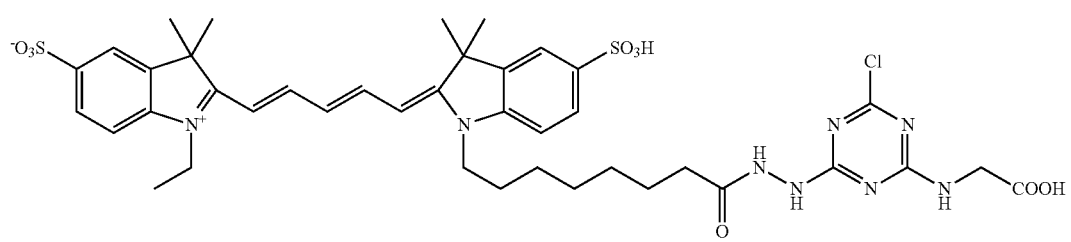
Compound 9
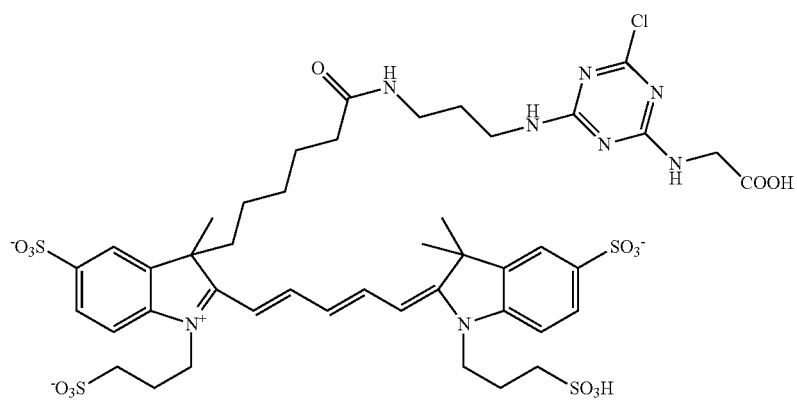

-continued
Compound 10
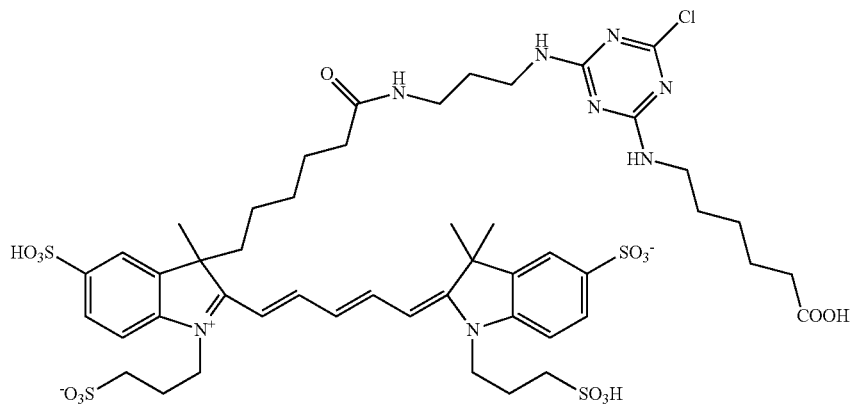
Compound 11
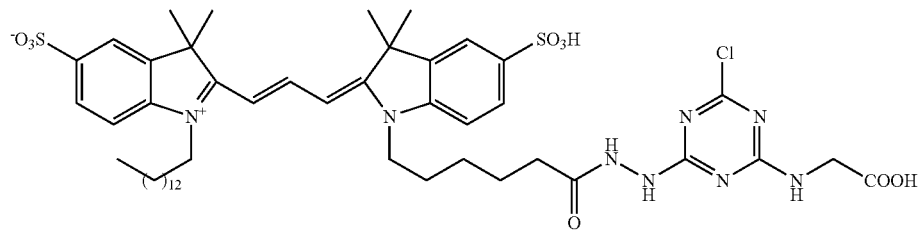
Compound 12
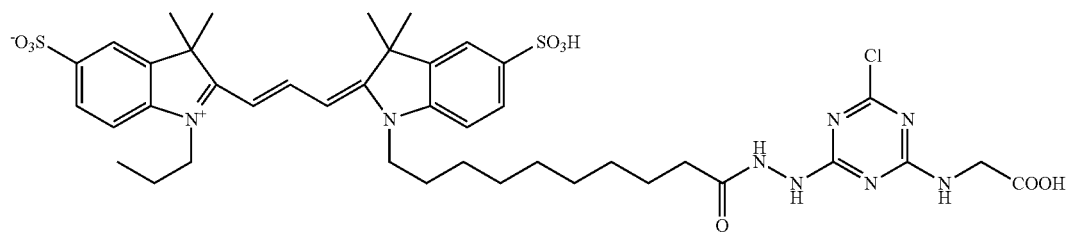
Compound 13
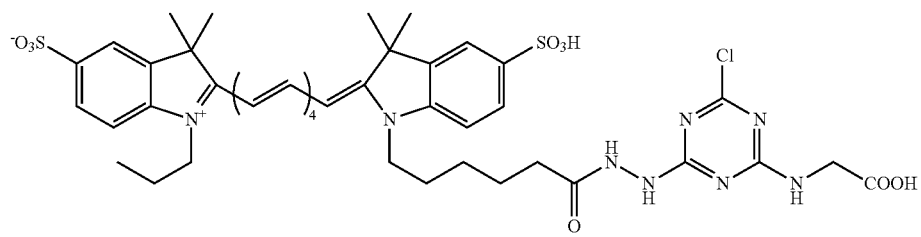
Compound 14
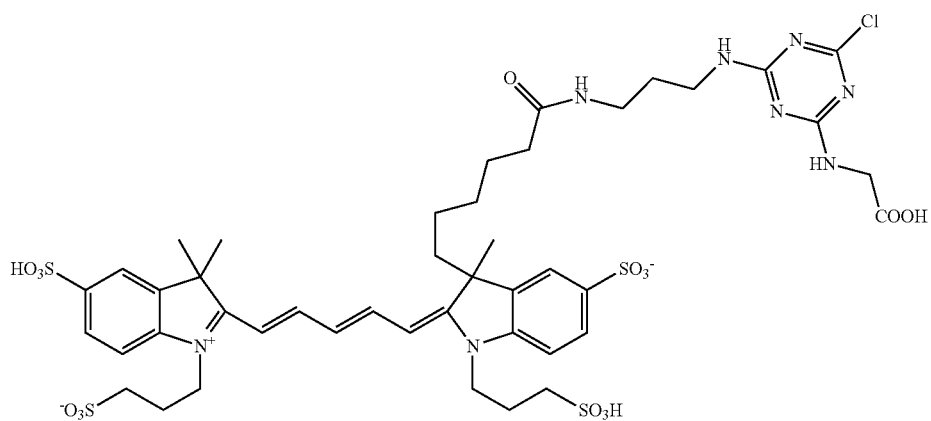

-continued
Compound 15
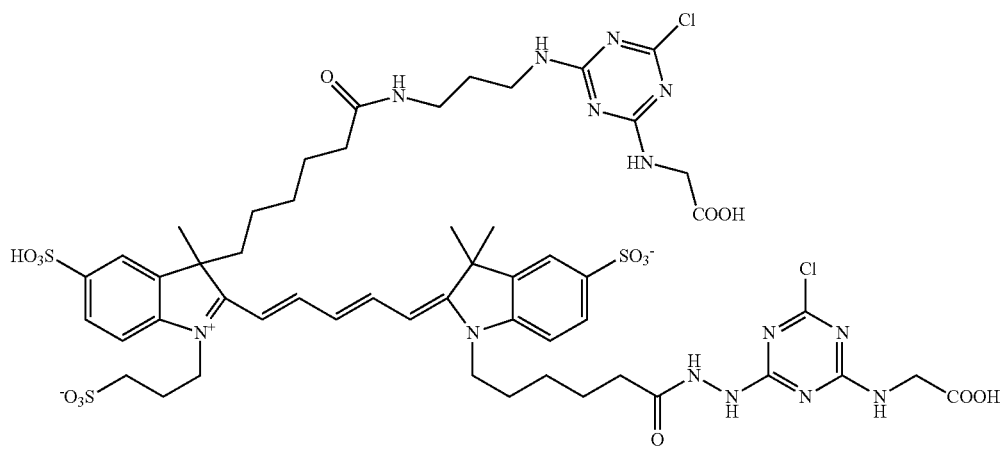
Compound 16
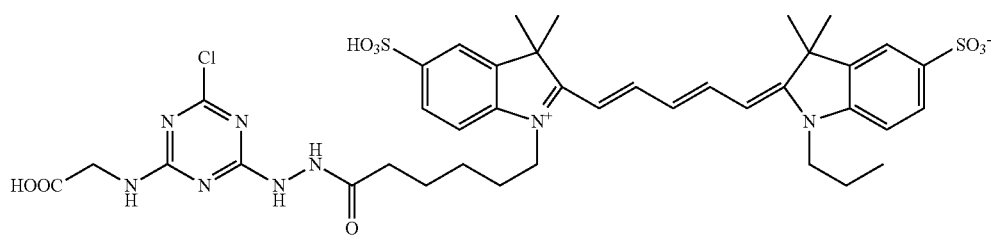
Compound 18
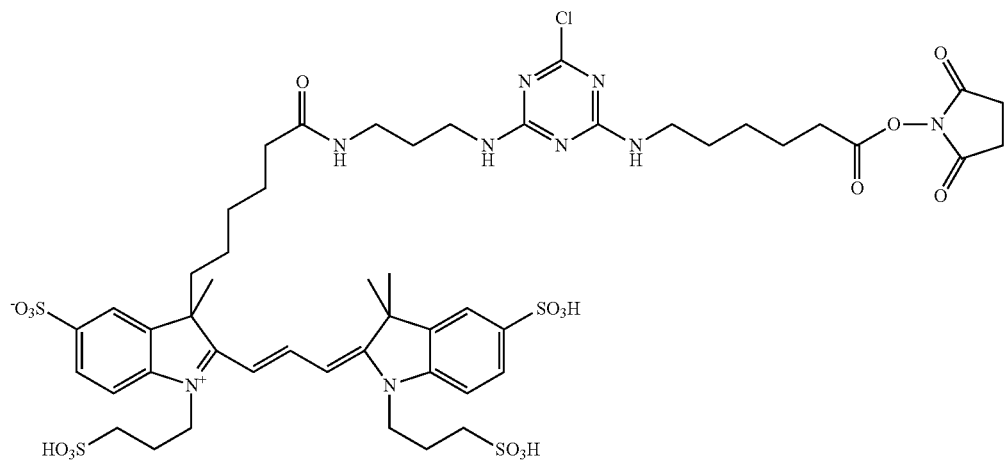
or
Compound 20
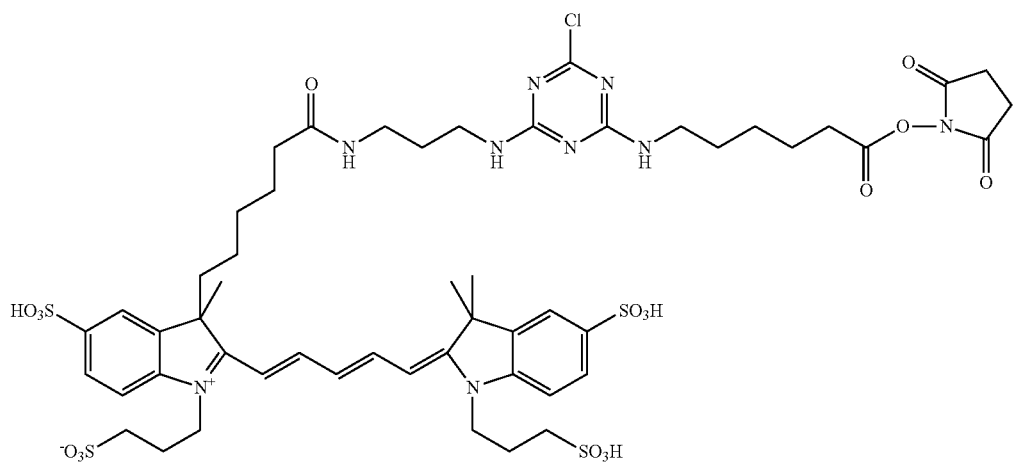

5. The fluorescent compound according to claim 1, which is used for labeling a target material selected from a fiber, biomolecule, nanoparticle and an organic compound.

6. The fluorescent compound according to claim 5, wherein the biomolecule is selected from the group consisting of proteins, peptides, carbohydrates, sugars, fats, antibodies, proteoglycans, glycoproteins and siRNA.

7. A method for preparing a fluorescent compound according to claim 1, which comprises producing a compound represented by the following [Chemical Formula 1] from a compound represented by the following [Chemical Formula 2]:

[Chemical Formula 2]

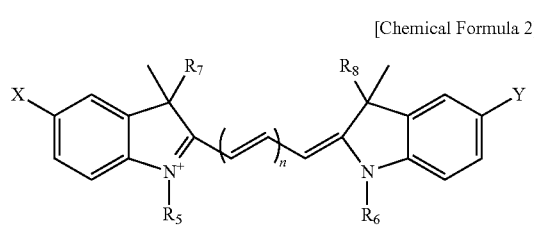

[Chemical Formula 1]

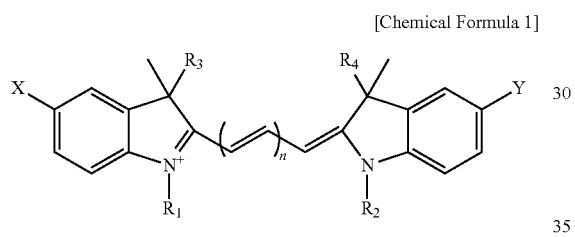

wherein X and Y are the same or different, and each is independently selected from H, —$SO_3^-$ and —$SO_3H$;

$R_1$ and $R_2$ are the same or different, and each is selected from $C_{1-7}$ alkyl, $C_{8-18}$ alkyl, —$(CH_2)_mSO_3^-$, —$(CH_2)_mSO_3H$, and

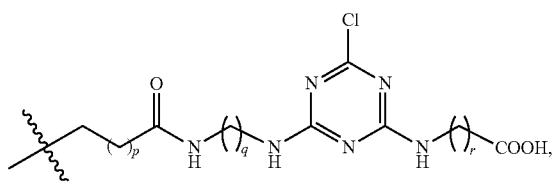

$R_3$ and $R_4$ are the same or different, and each is selected from $C_{1-7}$ alkyl, —$(CH_2)_mCOOZ_1$ and

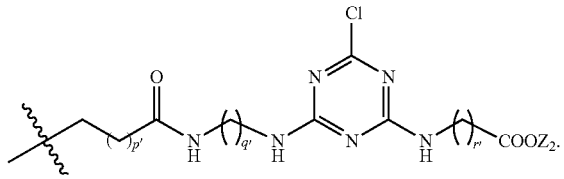

with the proviso that both of $R_3$ and $R_4$ cannot represent any one selected from —$(CH_2)_mCOOZ_1$ and

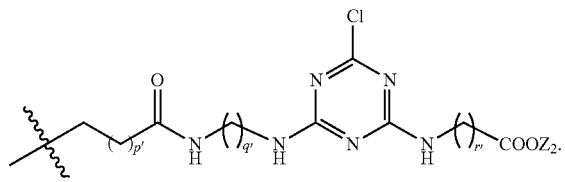

at the same time;

$R_5$ and $R_6$ are the same or different, and each is independently selected from $C_{1-7}$alkyl, $C_{8-18}$alkyl, —$(CH_2)_mSO_3^-$, —$(CH_2)_mSO_3H$ and

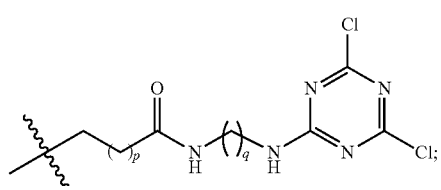

$R_7$ and $R_8$ are the same or different, and each is independently selected from $C_{1-7}$alkyl, —$(CH_2)_mCOOH$ and

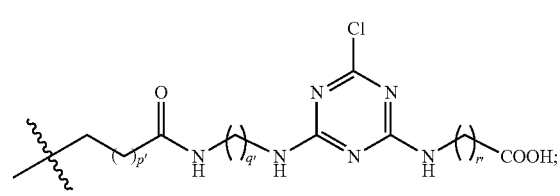

n is an integer of 1-6;
m is an integer of 1-7;
p is an integer of 1-10;
q is an integer of 0-6;
r is an integer of 1-10;
m' is an integer of 1-7;
p' is an integer of 1-10;
q' is an integer of 1-10; and
r' is an integer of 1-10.

8. The method for preparing a fluorescent compound according to claim 7, wherein the compound represented by [Chemical Formula 2] is obtained by reacting a compound represented by the following [Chemical Formula 3] with cyanuric chloride:

[Chemical Formula 3]

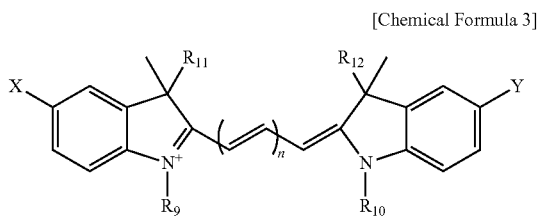

wherein X and Y are the same or different, and each is independently selected from H, —$SO_3^-$ and —$SO_3H$;

$R_9$ and $R_{10}$ are the same or different, and each is independently selected from $C_{1-7}$ alkyl, $C_{8-18}$ alkyl, —$(CH_2)_mSO_3^-$, —$(CH_2)_mSO_3H$ and

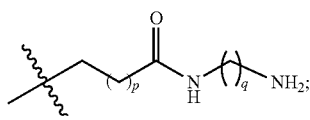

and $R_{11}$ and $R_{12}$ are the same or different, and each is independently selected from $C_{1-7}$ alkyl and

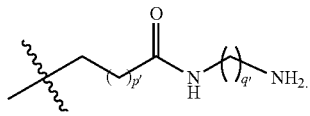

9. The method for preparing a fluorescent compound according to claim 8, wherein the compound represented by [Chemical Formula 3] is obtained by substituting a compound represented by the following [Chemical Formula 4] with an amine$C_{0-6}$alkylaminyl group:

[Chemical Formula 4]

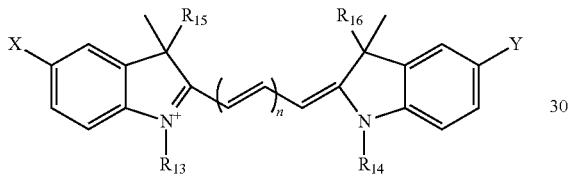

wherein X and Y are the same or different, and each is independently selected from H, —$SO_3^-$ and —$SO_3H$;
$R_{13}$ and $R_{14}$ are the same or different, and each is independently selected from $C_{1-7}$ alkyl, $C_{8-18}$ alkyl, —$(CH_2)_m SO_3^-$, —$(CH_2)_m SO_3H$ and

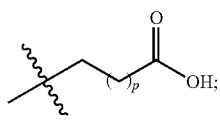

and $R_{15}$ and $R_{16}$ are the same or different, and each is independently selected from $C_{1-7}$ alkyl and

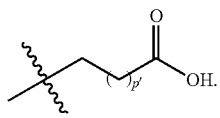

10. The method for preparing a fluorescent compound according to claim 9, the compound represented by [Chemical Formula 4] is obtained by refluxing a compound represented by the following [Chemical Formula 5] with a compound represented by the following [Chemical Formula 6] in the presence of a solvent containing acetic anhydride:

[Chemical Formula 5]

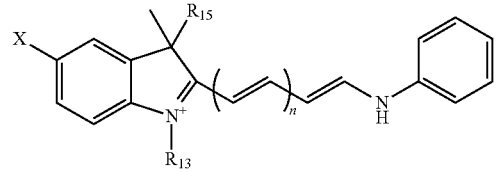

[Chemical Formula 6]

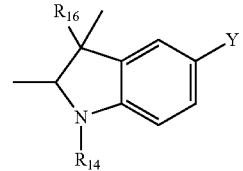

wherein X and Y are the same or different, and each is independently selected from H, —$SO_3^-$ and —$SO_3H$;
$R_{13}$ and $R_{14}$ are the same or different, and each is independently selected from $C_{1-7}$ alkyl, $C_{8-18}$ alkyl, —$(CH_2)_m SO_3^-$, —$(CH_2)_m SO_3H$ and

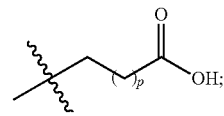

and $R_{15}$ and $R_{16}$ are the same or different, and each is independently selected from $C_{1-7}$ alkyl and

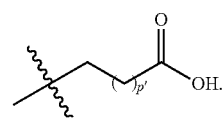

11. A contrast medium composition comprising the fluorescent compound represented by [Chemical Formula 1] as defined in claim 1 as an active ingredient.

12. A method for labeling a compound, which comprises binding the fluorescent compound represented by [Chemical Formula 1] as defined in claim 1 with a target material,
wherein the target material is at least one selected from a fiber, biomolecule, nanoparticle and an organic compound,
the target material comprises at least one functional group selected from amine, hydroxyl and thiol groups, and
the fluorescent compound as defined in claim 1 is bound with the functional group.

13. The method for labeling a compound according to claim 12, wherein the biomolecule is selected from the group consisting of proteins, peptides, carbohydrates, sugars, fats, antibodies, proteoglycan, glycoproteins and siRNA.

* * * * *